US009211529B2

(12) United States Patent
Fagan et al.

(10) Patent No.: US 9,211,529 B2
(45) Date of Patent: Dec. 15, 2015

(54) CONVERSION OF ETHANOL TO A REACTION PRODUCT COMPRISING 1-BUTANOL USING HYDROXYAPATITE CATALYSTS

(71) Applicant: E I DU PONT DE NEMOURS AND COMPANY, Wilmington, DE (US)

(72) Inventors: Paul Joseph Fagan, Wilmington, DE (US); Thomas G Calvarese, Wilmington, DE (US); Ronald James Davis, Christiana, PA (US); Ronnie Ozer, Arden, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 114 days.

(21) Appl. No.: 13/942,759

(22) Filed: Jul. 16, 2013

(65) Prior Publication Data
US 2013/0303362 A1 Nov. 14, 2013

Related U.S. Application Data

(62) Division of application No. 13/393,613, filed on Mar. 1, 2012.

(60) Provisional application No. 61/241,499, filed on Sep. 11, 2009.

(51) Int. Cl.
*C07C 31/02* (2006.01)
*C07C 31/12* (2006.01)
*C07C 29/34* (2006.01)
*B01J 27/182* (2006.01)
*B01J 27/138* (2006.01)
*B01J 27/18* (2006.01)
*B01J 27/185* (2006.01)
*B01J 37/06* (2006.01)
*B01J 37/08* (2006.01)
*B01J 27/186* (2006.01)
*B01J 27/198* (2006.01)
*B01J 35/00* (2006.01)
*B01J 35/10* (2006.01)
*B01J 37/03* (2006.01)

(52) U.S. Cl.
CPC ............ *B01J 27/182* (2013.01); *B01J 27/1806* (2013.01); *B01J 27/186* (2013.01); *B01J 27/1853* (2013.01); *B01J 27/198* (2013.01); *B01J 35/002* (2013.01); *B01J 35/1014* (2013.01); *B01J 37/06* (2013.01); *B01J 37/08* (2013.01); *C07C 29/34* (2013.01); *B01J 37/031* (2013.01)

(58) Field of Classification Search
USPC .............. 502/226, 104, 110, 208; 568/902.2
See application file for complete search history.

(56) References Cited

U.S. PATENT DOCUMENTS

| 3,558,716 | A | 1/1971 | Engelhardt et al. |
| 4,742,179 | A * | 5/1988 | Sanderson et al. ............ 568/913 |
| 6,323,383 | B1 | 11/2001 | Tsuchida et al. |
| 8,232,433 | B2 | 7/2012 | Onda et al. |
| 8,431,753 | B2 | 4/2013 | Ozer et al. |
| 2005/0053638 | A1 | 3/2005 | Tanaka et al. |
| 2005/0271571 | A1 | 12/2005 | Godber et al. |
| 2007/0255079 | A1 | 11/2007 | Tsuchida et al. |
| 2008/0025903 | A1 | 1/2008 | Cortright |
| 2008/0216391 | A1 | 9/2008 | Cortright et al. |
| 2008/0300434 | A1 | 12/2008 | Cortright et al. |
| 2008/0300435 | A1 | 12/2008 | Cortright et al. |
| 2009/0054707 | A1 | 2/2009 | Kourtakis et al. |
| 2009/0205246 | A1 | 8/2009 | Tsuchida et al. |

FOREIGN PATENT DOCUMENTS

| GB | 655864 | 8/1948 |
| GB | 949156 | 11/1962 |
| JP | 31005325 B4 | 7/1956 |
| JP | 2009220105 | 10/2009 |
| JP | 2009220105 A | 10/2009 |
| WO | 2008109877 A1 | 9/2008 |
| WO | 2009034719 A1 | 3/2009 |
| WO | 2009064825 A1 | 5/2009 |

(Continued)

OTHER PUBLICATIONS

Carlini et al., "Selective Synthesis of 2-ethyl-1-hexanol from n-butanol through the Guerbet Reaction by Using Bifunctional Catalysts Based on Copper or Palladium Precursors and Sodium Butoxide", J. of Molecular Catalysis A; Chemical 212 Issues 1-2, (2004) 65-70.
International Search Report and Written Opinion, International Application No. PCT/US10/48369, Mailed: Nov. 16, 2010.
Sugiyama, S; et al, "Comparison of Preparation Procedures of Barium Hydroxyapatites" Phos. Res. Bulletin. vol. 8, pp. 23-30 (1998).
Tsuchida, T.; et al. Ind. Eng. Chem. Research 47, pp. 1443-1452 (2008).
Wei, H.; et al., Catalysis Communications 9 pp. 516-521 (2008).
Tsuchida, T.; et al, Journal of the Japan Petroleum Institute, 52, (2), pp. 51-59 (2009).

(Continued)

*Primary Examiner* — Nyeemah A Grazier

(57) ABSTRACT

Catalytic processes to produce a reaction product comprising 1-butanol by contacting a reactant comprising ethanol with a catalyst composition under suitable reaction conditions are provided. The catalyst composition may comprise a hydroxyapatite of the Formula $(M_wM'_xM''_yM'''_z)_5(PO_4)_3(OH)$, wherein M is Mg; M' is Ca; M'' is Sr; M''' is Ba; w is any number between 0 and 1 inclusive; x is any number from 0 to less than 0.5; y is any number between 0 and 1 inclusive; z is any number between 0 and 1 inclusive; and $w+x+y+z=1$. Base-treated catalyst compositions may be used. Also provided are processes for contacting an initial catalyst composition comprising the hydroxyapatite with a base to produce a base-treated catalyst composition, and the base-treated catalyst compositions so obtained.

16 Claims, No Drawings

(56) References Cited

FOREIGN PATENT DOCUMENTS

WO  2011021232 A1  2/2011
WO  2011031029     3/2011

OTHER PUBLICATIONS

Logson, J.; "Guerbet Reaction", Kirk-Othmer Encyclopedia of Chemical Technology, John Wiley and Sons, Inc., NY, 2001. (not enclosed).

Yasukawa, Akemi; et al., "Preparations and Characterization of Barium-Strontium Hydroxyapatites", Journal of Colloid Interface Science; vol. 191, pp. 407-415 (1997).

Liou, S.C. et al., "Structural Characterization of nano-sized Calcium Deficient Apatite Powders"; Biomaterials, vol. 25, pp. 189-196, (2004).

Folger, H. Scott, (Elements of Chemical Reaction Engineering, $2^{nd}$ Edition, Prentice-Hall Inc., CA 1992). (Book).

Sugiyama, et al; "Effects of non-stoichiometry of Calcium and Strontium on the Oxidation of ethane in the presence of tetrachloromethane";Journal of Molecular Catalysis A: Chemical 135; pp. 199-208 (1998).

George, Grace., et al., "Preparation and Characterization of Phosphate and Arsenate Apatites . . . "; J. Material Science, vol. 22, pp. 2274-2276 (1987).

Fujino, Osamu.; "The Coprecipterization of Strontium with Hydroxyapatite"; Bulletin of the Chemical Society of Japan, vol. 48 (5), pp. 1455-1458 (1975).

\* cited by examiner

CONVERSION OF ETHANOL TO A REACTION PRODUCT COMPRISING 1-BUTANOL USING HYDROXYAPATITE CATALYSTS

CROSS-REFERENCE TO RELATED APPLICATIONS

This application is a divisional of co-pending U.S. application Ser. No. 13/393,613 filed on Mar. 1, 2012.

FIELD OF THE INVENTION

The present invention relates to processes for the catalytic conversion of ethanol to a reaction product comprising 1-butanol using hydroxyapatite catalyst compositions. The present invention also relates to processes for preparing the catalyst, and to the catalyst compositions so obtained.

BACKGROUND

Efforts directed at improving air quality and increasing energy production from renewable resources have resulted in renewed interest in alternative fuels, such as ethanol and butanol, that might replace gasoline and diesel fuel, or be used as additives in gasoline and diesel fuel.

Methods for producing 1-butanol from ethanol are known. For example, 1-butanol can be prepared by condensation from ethanol over basic catalysts at high temperature using the so-called "Guerbet Reaction" (see for example, J. Logsdon in Kirk-Othmer Encyclopedia of Chemical Technology, John Wiley and Sons, Inc., New York, 2001).

U.S. Pat. No. 6,323,383 describes a method of synthesizing 1-butanol from ethanol using a catalyst made of calcium phosphates, particularly low-crystalline calcium phosphates singly or as a mixture, wherein the Ca/P mol ratio is adjusted to from 1.4 to 1.8, as it is, or a catalyst by carrying an activation metal or the oxide thereof on the catalyst such that the (Ca+metal)/P mol ratio becomes from 1 to 2.

Published US Patent Application 2007/0255079 A1 discloses a process for producing, from ethanol as a raw material, higher molecular weight alcohols having an even number of carbon atoms, such as 1-butanol, hexanol, octanol and decanol. The higher molecular weight alcohols are produced from ethanol using calcium phosphate-based compounds such as hydroxyapatite $Ca_{10}(PO_4)_6(OH)_2$, tricalcium phosphate $Ca_3(PO_4)_2$, calcium monohydrogen phosphate $CaHPO_4\cdot(0\text{-}2)H_2O$, calcium diphosphate $Ca_2P_2O_7$, octacalcium phosphate $Ca_8H_2(PO_4)_6\cdot5H_2O$, tetracalcium phosphate $Ca_4(PO_4)_2O$, or amorphous calcium phosphate $Ca_3(PO_4)_2\cdot nH_2O$ as a catalyst, the contact time being 0.4 second or longer.

Hydroxyapatite compositions comprising an alkaline earth metal other than calcium, or a mixture of more than one alkaline earth metal, are also known. For example, a comparison of preparation procedures of to barium hydroxyapatites has been reported (S. Sugiyama, T. Nakanishi, H. Hayashi, J. B. Moffat, Phos. Res. Bull. Vol. 8, pp 23-30 (1998). The preparation and characterization of phosphate and arsenate apatites of strontium and their solid solutions is described (G. George, S. K. Gupta, P. V. R. Rao, T. S. B. Narasaraju J. Mat. Sci. Vol. 22, pp 2274-2276 (1987)). The preparation of barium-strontium hydroxyapatites is described by A. Yasukawa et al. (A. Yasukawa, M. Kidokoro, K. Kandori, T. Ishikawa, J. Colloid Interface Sci., Vol. 191, pp 407-415 (1997)). The coprecipitation of strontium with hydroxyapatite (O. Fujino, Bull. Chem. Soc. Jpn. Vol. 48, pp 1455-1458 (1975)), and the preparation of hydroxyapatite loaded with strontium (S.-C. Liou, S.-Y. Chen, H.-Y. Lee, J.-S. Bow, Biomaterials, Vol. 25, pp 189-196, (2004)) have also been disclosed. The latter two references refer to mixed calcium/strontium hydroxyapatites.

New catalyst compositions useful in a process for producing butanol from a reactant stream comprising ethanol are continually sought. Catalyst compositions which can provide high conversions of ethanol to butanol are desired. Also desired are catalyst compositions which provide good selectivity to butanol, as well as catalyst compositions having long catalytic lifetimes. Additionally, processes to produce butanol and which employ such new catalyst compositions are desired for the economic benefits they can offer.

SUMMARY OF THE INVENTION

The present invention provides catalytic processes for producing a reaction product comprising 1-butanol from a reactant comprising ethanol, using catalyst compositions comprising certain hydroxyapatite compositions. The present invention also provides processes for producing a base-treated catalyst composition, as well as the catalyst compositions so obtained.

In one aspect, the present invention is a process comprising the step of contacting a reactant comprising ethanol with a catalyst composition under suitable reaction conditions to produce a reaction product comprising 1-butanol, wherein;

(i) the suitable reaction conditions include a temperature of about 150° C. to about 500° C. and a pressure from about 0.1 MPa to about 20.7 MPa; and (ii) the catalyst composition comprises a hydroxyapatite of Formula (I):

$$(M_w M'_x M''_y M'''_z)_5(PO_4)_3(OH) \quad (I)$$

wherein
M is Mg;
M' is Ca;
M" is Sr;
M''' is Ba;
w is any number between 0 and 1 inclusive;
x is any number from 0 to less than 0.5;
y is any number between 0 and 1 inclusive;
z is any number between 0 and 1 inclusive;
and w+x+y+z=1.

In one aspect, the present invention is a process comprising the step of contacting an initial catalyst composition comprising a hydroxyapatite of Formula (III):

$$(M_m M'_n M''_p M'''_q)_5(PO_4)_3(OH) \quad (III)$$

where
M is Mg;
M' is Ca;
M" is Sr;
M''' is Ba;
m is any number between 0 and 1 inclusive;
n is any number between 0 and 1 inclusive;
p is any number between 0 and 1 inclusive;
q is any number between 0 and 1 inclusive;
and m+n+p+q=1
with a base at a temperature from about 25° C. to about 300° C. for a time of about 1 minute to about 24 hours to produce a base-treated catalyst composition.

In one aspect, the present invention is a process comprising the step of contacting a reactant comprising ethanol with a base-treated catalyst composition under suitable reaction conditions to produce a reaction product comprising 1-butanol;

wherein the suitable reaction conditions include a temperature of about 150° C. to about 500° C. and a pressure from about 0.1 MPa to about 20.7 MPa; and wherein the base-treated catalyst composition is obtained by treating an initial catalyst composition comprising a hydroxyapatite of Formula (III):

$$(M_mM'_nM''_pM'''_q)_5(PO_4)_3(OH) \quad (III)$$

wherein
M is Mg;
M' is Ca;
M" is Sr;
M"' is Ba;
m is any number between 0 and 1 inclusive;
n is any number between 0 and 1 inclusive;
p is any number between 0 and 1 inclusive;
q is any number between 0 and 1 inclusive;
and m+n+p+q=1 with a base at a treatment temperature from about 25° C. to about 300° C. for a treatment time of about 1 minute to about 24 hours, and optionally washing the isolated base-treated catalyst composition with a minimal amount of water.

In one aspect, the present invention is a process comprising the step:

contacting a reactant comprising ethanol with a base-treated catalyst composition under suitable reaction conditions to produce a reaction product comprising 1-butanol;

wherein the suitable reaction conditions include a temperature of about 150° C. to about 500° C. and a pressure from about 0.1 MPa to about 20.7 MPa; and wherein the base-treated catalyst composition is obtained by treating an initial catalyst composition comprising a hydroxyapatite of Formula (I):

$$(M_wM'_xM''_yM'''_z)_5(PO_4)_3(OH) \quad (I)$$

wherein
M is Mg;
M' is Ca;
M" is Sr;
M"' is Ba;
w is any number between 0 and 1 inclusive;
x is any number from 0 to less than 0.5;
y is any number between 0 and 1 inclusive;
z is any number between 0 and 1 inclusive;
and w+x+y+z=1 with a base at a treatment temperature from about 25° C. to about 300° C. for a treatment time of about 1 minute to about 24 hours, and optionally washing the base-treated catalyst composition with a minimal amount of water.

In one aspect, the present invention is a composition, the composition comprising a base-treated catalyst derived from a hydroxyapatite of the Formula $(M_mM'_nM''_pM'''_q)_5(PO_4)_3(OH)$ as defined below;
wherein the composition is obtained by
a) providing an initial catalyst composition comprising a hydroxyapatite of Formula (III):

$$(M_mM'_nM''_pM'''_q)_5(PO_4)_3(OH); \quad (III)$$

wherein
M is Mg;
M' is Ca;
M" is Sr;
M"' is Ba;
m is any number between 0 and 1 inclusive;
n is any number between 0 and 1 inclusive;

p is any number between 0 and 1 inclusive;
q is any number between 0 and 1 inclusive;
and m+n+p+q=1; and b) treating the initial catalyst composition with a base comprising an aqueous solution of a metal hydroxide $Q(OH)_f$, where f is 1 to 3 inclusive and Q is at least one metal selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb at a temperature from about 25° C. to about 300° C. and for a time of about 1 minute to about 24 hours to produce a composition comprising a base-treated catalyst derived from a hydroxyapatite of Formula (III).

In one aspect, the present invention is a composition, the composition comprising a base-treated catalyst derived from a hydroxyapatite of the Formula $(M_wM'_xM''_yM'''_z)_5(PO_4)_3(OH)$ as defined below,
wherein the composition is obtained by
a) providing an initial catalyst composition comprising a hydroxyapatite of Formula (I);

$$(M_wM'_xM''_yM'''_z)_5(PO_4)_3(OH) \quad (I);$$

wherein
M is Mg;
M' is Ca;
M" is Sr;
M"' is Ba;
w is any number between 0 and 1 inclusive;
x is any number from 0 to less than 0.5;
y is any number between 0 and 1 inclusive;
z is any number between 0 and 1 inclusive;
and w+x+y+z=1; and b) treating the initial catalyst composition with a base comprising an aqueous solution of a metal hydroxide $Q(OH)_f$, where f is 1 to 3 inclusive and Q is at least one metal selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb at a temperature from about 25° C. to about 300° C. and for a time of about 1 minute to about 24 hours to produce a composition comprising a base-treated catalyst derived from a hydroxyapatite of Formula (I).

BRIEF DESCRIPTION OF THE FIGURES

FIG. 1 shows a representation of a transmission electron microscopy image of the nanocrystalline catalyst composition prepared in Example 5.

FIG. 2 shows a representation of a transmission electron microscopy image of the nanocrystalline catalyst composition prepared in Example 5.

FIG. 3 shows the Electron Dispersion Spectrum of the sample of the nanocrystalline catalyst composition prepared in Example 3 and shown in FIG. 2.

FIG. 4 shows the total conversion of ethanol to products as a function of time for the catalyst composition prepared and evaluated in Example 15.

DETAILED DESCRIPTION OF THE INVENTION

The present invention relates to processes for producing a base-treated catalyst composition, and the base-treated catalyst compositions derived from these processes. The present invention also relates to catalytic processes for producing a reaction product comprising 1-butanol from a reactant comprising ethanol, using catalyst compositions comprising certain hydroxyapatite compositions or catalyst compositions which have haven treated with a base. Useful applications for the 1-butanol, which can be separated from the reaction product, include as an additive or blend component to diesel fuel. Ethanol is produced from renewable resources such as corn, sugar cane, or cellulosic feeds, In countries such as Brazil where ethanol production is operated at large scale, the ability to produce 1-butanol from ethanol offers an advantage.

Where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

Where a range of numerical values is recited herein, unless otherwise stated, the range is intended to include the endpoints thereof, and all integers and fractions within the range. It is not intended that the scope of the invention be limited to the specific values recited when defining a range.

The following definitions are used herein and should be referred to for interpretation of the claims and the specification.

The term "ethanol conversion" means the chemical reaction of ethanol to another compound.

The term "unreacted ethanol" means ethanol which has not been chemically reacted to another compound.

The term "elapsed time" means reaction time measured from the time when the reaction product comprising 1-butanol first exits the reactor.

The term "contacting" means bringing at least two things, such as an initial catalyst composition and a base, into physical contact.

The terms "Guerbet alcohol products" or "Guerbet alcohols" mean one or more alcohols produced by the Guerbet synthesis, wherein a primary or secondary alcohol having a methylene group at the α-position is condensed with itself, or with another alcohol also having a methylene group, to form a higher alcohol containing twice the number of carbon atoms of the single starting alcohol or, in the case of mixed alcohols, the sum of the number of carbon atoms in each reacting pair of alcohols. 1-Butanol is a Guerbet alcohol product of ethanol.

The term "base catalyst" means either a substance which has the ability to accept protons as defined by Brönsted, or a substance which has an unshared electron pair with which it can form a covalent bond with an atom, molecule or ion as defined by Lewis.

The term "wt %" means weight percent.
The term "° C." means degrees Celsius.
The term "mg" means milligram(s).
The term "g" means gram(s).
The term "min" means minute(s).
The term "h" means hour(s).
The term "mL" means milliliter(s).
The term "M" means molar.
The term "cm" means centimeter(s).
The term "MPa" means mega Pascal.
The term "GC" means gas chromatography.
The term "rpm" means revolutions per minute.

Catalyst Composition:

In one embodiment of the process to produce a reaction product comprising 1-butanol, the catalyst composition comprises at least one hydroxyapatite based on unary, binary, tertiary, and quaternary combinations of magnesium, calcium, strontium, and barium cations. The catalyst composition comprises a hydroxyapatite of Formula (I):

$$(M_wM'_xM''_yM'''_z)_5(PO_4)_3(OH) \tag{I}$$

where
M is Mg;
M' is Ca;
M" is Sr;
M'" is Ba;
w is any number between 0 and 1 inclusive;
x is any number from 0 to less than 0.5;
y is any number between 0 and 1 inclusive;
z is any number between 0 and 1 inclusive;
and w+x+y+z=1.

With respect to M, M', M", and M'", each of the metals is optional in the catalyst composition to the extent that at least one of the metals has to be present to conform to the above formulation.

In one embodiment, the catalyst composition comprises a hydroxyapatite of Formula (I) wherein w is 1, x is 0, y is 0, and z is 0. In one embodiment, the catalyst composition comprises a hydroxyapatite of Formula (I) wherein w is 0, x is 0, y is 1, and z is 0. In one embodiment, the catalyst composition comprises a hydroxyapatite of Formula (I) wherein w is 0, x is 0, y is 0, and z is 1.

In one embodiment, the catalyst composition comprises a hydroxyapatite of Formula (I) wherein w is any number between 0 and 1 inclusive; x is any number from 0 to less than 0.5; y is 0; and z is 0. In one embodiment, the catalyst composition comprises a hydroxyapatite of Formula (I) wherein w is any number between 0 and 1 inclusive; x is 0; y is any number between 0 and 1 inclusive; and z is 0. In one embodiment, the catalyst composition comprises a hydroxyapatite of Formula (I) wherein w is any number between 0 and 1 inclusive; x is 0; y is 0; and z is any number between 0 and 1 inclusive. In one embodiment, the catalyst composition comprises a hydroxyapatite of Formula (I) wherein w is 0; x is any number from 0 to less than 0.5; y is any number between 0 and 1 inclusive; and z is 0. In one embodiment, the catalyst composition comprises a hydroxyapatite of Formula (I) w is 0; x is any number from 0 to less than 0.5; y is 0; and z is any number between 0 and 1 inclusive. In one embodiment, the catalyst composition comprises a hydroxyapatite of Formula (I) wherein w is 0; x is 0; y is any number between 0 and 1 inclusive; and z is any number between 0 and 1 inclusive.

The catalyst composition may optionally further comprise at least one metal phosphate of Formula (II):

$$(M_aM'_bM''_cM'''_d)_3(PO_4)_2 \tag{II}$$

where
M is Mg;
M' is Ca;
M" is Sr;
M'" is Ba;
a is any number between 0 and 1 inclusive;
b is any number between 0 and 1 inclusive;
c is any number between 0 and 1 inclusive;
d is any number between 0 and 1 inclusive;
and a+b+c+d=1.

With respect to M, M', M", and M'", each of the metals is optional in the catalyst composition to the extent that at least one of the metals has to be present to conform to the above formulation.

The metal phosphate may comprise, for example, Mg, Ca, Sr, and Ba, or any three of these elements, or any two of these elements, or only one of these elements. In one embodiment, the catalyst composition comprises a metal phosphate of Formula (II) where a is 1, b is 0, c is 0, and d is 0. In one embodiment, the catalyst composition comprises a metal phosphate of Formula (II) where a is 0, b is 1, c is 0, and d is 0. In one embodiment, the catalyst composition comprises a metal phosphate of Formula (II) where a is 0, b is 0, c is 1, and d is 0. In one embodiment, the catalyst composition comprises a metal phosphate of Formula (II) where a is 0, b is 0, c is 0, and d is 1.

In one embodiment, the catalyst composition comprises a metal phosphate of Formula (II) wherein a is any number between 0 and 1 inclusive; b is any number between 0 and 1 inclusive; c is 0; and d is 0. In one embodiment, the catalyst composition comprises a metal phosphate of Formula (II) wherein a is any number between 0 and 1 inclusive; b is 0; c is any number between 0 and 1 inclusive; and d is 0. In one embodiment, the catalyst composition comprises a metal phosphate of Formula (II) wherein a is any number between 0 and 1 inclusive; b is 0; c is 0; and d is any number between 0 and 1 inclusive. In one embodiment, the catalyst composition comprises a metal phosphate of Formula (II) wherein a is 0; b is any number between 0 and 1 inclusive; c is any number between 0 and 1 inclusive; and d is 0. In one embodiment, the catalyst composition comprises a metal phosphate of Formula (II) a is 0; b is any number between 0 and 1 inclusive; c is 0; and d is any number between 0 and 1 inclusive. In one embodiment, the catalyst composition comprises a metal phosphate of Formula (II) wherein a is 0; b is 0; c is any number between 0 and 1 inclusive; and d is any number between 0 and 1 inclusive.

The catalyst composition may optionally further comprise at least one metal or metal on selected from the lanthanides, the alkali metals, and the transition metals. In one embodiment, the catalyst composition may further comprise at least one metal or metal on selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb. In one embodiment, the catalyst composition may further comprise at least one metal or metal on selected from the group consisting of Li, Na, K, Rb, Cs, Sc, Y, Lu, Ti, V. Cr, Mn, Fe, Co, Ni, Cu, Zn, Zr, Nb, Mo, Ru, Rh, Pd, Ag, Ta, W, Re, Ir, Pt, Au, La, Ce, and Yb. In one embodiment, the optional metal(s) or metal ion(s) may be present in an amount less than about 50 mole percent of the total metals $[M_w + M'_x + M''_y + M'''_z]$. In one embodiment, the optional metal(s) or metal ion(s) may be present in an amount less than about 30 mole percent of the total metals $[M_w + M'_x + M''_y + M'''_z]$. In one embodiment, the optional metal(s) may be present in an amount less than about 15 mole percent of the total metals $[(M_w + M'_x + M''_y + M'''_z]$. The optional metal(s) or metal ion(s) may be incorporated into the bulk hydroxyapatite during its synthesis, or may be added to the surface of the catalyst composition by methods known in the art.

The catalyst composition may further comprise at least one anionic additive selected from the group consisting of carbonate, silicate, aluminate, arsenate, vanadate, sulfate, and borate. Other additives may be used so long as the presence of the additive is not deleterious to the catalyst composition or its use in the process. In one embodiment, the additive may be present in an amount less than about 10 mole percent of the total metals $[M_w + M'_x + M''_y + M'''_z]$. In one embodiment, at least some of the phosphate groups of the hydroxyapatite may be substituted by one or more of these anionic additives, for example by arsenate or vanadate.

Catalyst compositions comprising a hydroxyapatite of Formula (I) can be obtained as nanocrystalline solids. The particles in the nanocrystalline catalyst composition can have dimensions which range from about 10 nm to about 50 nm in length in the shortest dimension and about 50 nm to about 500 nm in length in the longest dimension, for example from about 10 nm to about 50 nm in length in the shortest dimension and about 80 nm to about 400 nm in length in the longest dimension. Nanocrystalline catalysts can be advantageous due to their higher surface area which increases the amount of conversion per unit mass of catalyst.

The catalyst compositions can have surface areas of greater than about 2 meters squared per gram. In one embodiment, the catalyst compositions can have a surface area greater than about 5 meters squared per gram. In one embodiment, the catalyst compositions can have a surface area greater than about 10 meters squared per gram. Higher surface area is generally desirable for catalyst compositions as higher surface area can provide higher catalytic activity on a constant weight basis.

The catalyst composition comprising a hydroxyapatite of Formula (I) can be synthesized by the following methods. In one method, an aqueous salt solution containing one or more divalent metals selected from the group consisting of magnesium, calcium, strontium, and barium is prepared. The molar ratio of the divalent metals is selected to satisfy the stoichiometry of the hydroxyapatite of Formula (I). Preferred salts are metal nitrates, metal sulfates, and metal carboxylates. Most preferred are metal carboxylates. To the stirred aqueous metal salt solution are simultaneously added concentrated ammonium hydroxide (neat or as an about 5 M to about 15 M solution) and concentrated phosphoric acid (neat or as an about 2 M to about 15 M solution). The reagents can be added dropwise, or via a liquid pump at a rate of from about 1 to 10 mL/min, preferably from about 1 to 6 mL/min. The rates of ammonium hydroxide and phosphoric acid addition are adjusted to maintain a pH greater than about 10 in the reaction volume during addition. Temperatures during synthesis of the catalyst composition can be from about 0° C. to about 250° C. If necessary, suitable pressure equipment can be used. Agitation of the reaction medium can be accomplished with a magnetic stirring bar, or overhead mechanical stirrer. After completion of addition, the reaction can be stirred for a period of time from about 0.5 h to about 24 h, for example from about 1 h to 4 h. The solid that precipitates can be isolated by centrifugation or filtration. The solids can be optionally washed with water after isolation. After drying to remove water, the solid can be calcined at from about 400 to 800° C., preferably from 500 to 700° C., for a period of time from about 1 h to 24 h, for example about 2 h to –15, or for example from about 2 h to 10 h, in an oven in air.

Alternatively, an aqueous metal hydroxide or metal oxide solution or slurry containing one or more divalent metals selected from the group consisting of magnesium, calcium, strontium, and barium is prepared. The molar ratio of the divalent metals is selected to satisfy the stoichiometry of the hydroxyapatite of Formula (I), To the stirred aqueous metal hydroxide solution (from about 0.02 to 3 M, preferably from 0.4 to 2.2 M) is added concentrated phosphoric acid (neat or as an about 0.1 M to about 15 M solution), Phosphoric acid can be added dropwise, or via a liquid pump at a rate of from about 1 to 10 mL/min, preferably from about 1 to 6 mL/min. The pH of the reaction mixture is maintained at >10, preferably >12 during the addition of phosphoric acid. Excess metal hydroxide can be maintained in solution at the end of the reaction. Temperatures during synthesis of the catalyst composition can be from about 0° C. to about 250° C. If necessary, suitable pressure equipment can be used. Agitation of the reaction medium can be accomplished with a magnetic stirring bar, or overhead mechanical stirrer. After completion of addition, the reaction can be stirred for a period of time from about 0.5 h to 24 h, for example from about 1 h to 4 h. The solid that precipitates can be isolated by centrifugation or filtration. The solids can be optionally washed with water after isolation. After drying to remove water, the solid can be calcined at from about 400 to 800° C., preferably from 500 to 700° C., for a period of time from about 1 h to 24 h, for example about 2 h to 15 h, or for example 2 h to 10 h, in an oven in air.

Other synthetic methods known to those of skill in the art may also be used to prepare the catalyst compositions.

Metal phosphates of Formula (II) may be generated during the calcination procedures as an admixture with a hydroxyapatite of Formula (I). The presence of metal phosphates can be determined by X-ray powder diffraction analysis of the catalyst composition. In one embodiment, the catalyst composition may comprise from about 0 weight percent to about 25 weight percent metal phosphate. The amount of metal phosphate may optionally be greater than 25 weight percent.

Optionally, at least one metal or metal on selected from the lanthanides, the alkali metals, and the transition metals can be added to the catalyst composition during the synthesis procedure. The metal or metal ion may be added, for example, by reacting or physically mixing the catalyst composition with metals, metal compounds, or metal salts before or after the calcination procedure. Alternatively, the catalyst composition may be reacted with metal compounds or salts in appropriate solvents, before or after the calcination procedure. At least one additive selected from the group consisting of carbonate, silicate, aluminate, arsenate, vanadate, sulfate, and borate may be added to the catalyst composition in a similar manner. The optional metal(s) and/or additive may be incorporated into the bulk hydroxyapatite during its synthesis, or may be added to the surface of the initial catalyst composition.

Preparation of the catalyst composition for use in a process to produce 1-butanol can further include pelletizing the solid catalyst composition, crushing and sieving the material, and optionally calcining the material at a temperature from about 400 to 800° C., preferably from 500 to 700° C., for a period of time from about 1 h to 24 h, for example about 2 h to 15 h, or for example 2 to 10 h, in an oven in air.

Base-Treated Catalyst Composition:

Base treatment of a catalyst composition comprising a hydroxyapatite of Formula (I) as described herein above or a hydroxyapatite of Formula (III) as described herein below is expected to provide a catalyst composition having better performance for producing 1-butanol, for example a catalyst composition providing higher activity and/or higher selectivity to 1-butanol.

In one embodiment of the process to produce a reaction product comprising 1-butanol, the catalyst composition comprises a base-treated catalyst composition obtained by contacting an initial catalyst composition comprising a hydroxyapatite of Formula (I) with a base.

The initial catalyst composition comprises at least one hydroxyapatite based on unary, binary, tertiary, and quaternary combinations of magnesium, calcium, strontium, and barium cations. The catalyst composition comprises a hydroxyapatite of Formula (I).

In one embodiment, the catalyst composition comprises a hydroxyapatite of Formula (I) wherein w is 1, x is 0, y is 0, and z is 0. In one embodiment, the catalyst composition comprises a hydroxyapatite of Formula (I) wherein w is 0, x is 0, y is 1, and z is 0. In one embodiment, the catalyst composition comprises a hydroxyapatite of Formula (I) wherein w is 0, x is 0, y is 0, and z is 1.

In one embodiment, the catalyst composition comprises a hydroxyapatite of Formula (I) wherein w is any number between 0 and 1 inclusive; x is any number from 0 to less than 0.5; y is 0; and z is 0. In one embodiment, the catalyst composition comprises a hydroxyapatite of Formula (I) wherein w is any number between 0 and 1 inclusive; x is 0; y is any number between 0 and 1 inclusive; and z is 0. In one embodiment, the catalyst composition comprises a hydroxyapatite of Formula (I) wherein w is any number between 0 and 1 inclusive; x is 0; y is 0; and z is any number between 0 and 1 inclusive. In one embodiment, the catalyst composition comprises a hydroxyapatite of Formula (I) wherein w is 0; x is any number from 0 to less than 0.5; y is any number between 0 and 1 inclusive; and z is 0. In one embodiment, the catalyst composition comprises a hydroxyapatite of Formula (I) w is 0; x is any number from 0 to less than 0.5; y is 0; and z is any number between 0 and 1 inclusive. In one embodiment, the catalyst composition comprises a hydroxyapatite of Formula (I) wherein w is 0; x is 0; y is any number between 0 and 1 inclusive; and z is any number between 0 and 1 inclusive.

In another embodiment of the process to produce a reaction product comprising 1-butanol, the catalyst composition comprises a base-treated catalyst composition obtained by contacting an initial catalyst composition comprising a hydroxyapatite of Formula (III) with a base, The initial catalyst composition comprises at least one hydroxyapatite based on unary, binary, tertiary, and quaternary combinations of magnesium, calcium, strontium, and barium cations. The initial catalyst composition comprises a hydroxyapatite of Formula (III):

$$(M_mM'_nM''_pM'''_q)_5(PO_4)_3(OH) \quad (III)$$

where
M is Mg;
M' is Ca;
M'' is Sr;
M''' is Ba;
m is any number between 0 and 1 inclusive;
n is any number between 0 and 1 inclusive;
p is any number between 0 and 1 inclusive;
q is any number between 0 and 1 inclusive;
and m+n+p+q=1.

With respect to M, M', M'', and M''', each of the metals is optional in the catalyst composition to the extent that at least one of the metals has to be present to conform to the above formulation.

In one embodiment, the initial catalyst composition comprises a hydroxyapatite of Formula (III) where m is 1, n is 0, p is 0, and q is 0. In one embodiment, the initial catalyst composition comprises a hydroxyapatite of Formula (III) where m is 0, n is 1, p is 0, and q is 0. In one embodiment, the initial catalyst composition comprises a hydroxyapatite of Formula (III) where m is 0, n is 0, p is 1, and q is 0. In one embodiment, the initial catalyst composition comprises a hydroxyapatite of Formula (III) where m is 0, n is 0, p is 0, and q is 1.

In one embodiment, the initial catalyst composition comprises a hydroxyapatite of Formula (III) wherein m is any number between 0 and 1 inclusive; n is any number between 0 and 1 inclusive; p is 0; and q is 0. In one embodiment, the initial catalyst composition comprises a hydroxyapatite of Formula (III) wherein m is any number between 0 and 1 inclusive; n is 0; p is any number between 0 and 1 inclusive; and q is 0. In one embodiment, the initial catalyst composition comprises a hydroxyapatite of Formula (III) wherein m is any number between 0 and 1 inclusive; n is 0; p is 0; and q is any number between 0 and 1 inclusive. In one embodiment, the initial catalyst composition comprises a hydroxyapatite of Formula (III) wherein m is 0; n is any number between 0 and 1 inclusive; p is any number between 0 and 1 inclusive; and q is 0. In one embodiment, the initial catalyst composition comprises a hydroxyapatite of Formula (III) m is 0; n is any number between 0 and 1 inclusive; p is 0; and q is any number between 0 and 1 inclusive. In one embodiment, the initial catalyst composition comprises a hydroxyapatite of Formula (III) wherein m is 0; n is 0; p is any number between 0 and 1 inclusive; and q is any number between 0 and 1 inclusive.

The initial catalyst composition comprising a hydroxyapatite of Formula (I) or Formula (III) may optionally further comprise at least one metal phosphate of Formula (II).

The metal phosphate may comprise, for example, Mg, Ca, Sr, and Ba, or any three of these elements, or any two of these elements, or only one of these elements. In one embodiment, the initial catalyst composition comprises a metal phosphate of Formula (II) where a is 1, b is 0, c is 0, and d is 0. In one embodiment, the initial catalyst composition comprises a metal phosphate of Formula (II) where a is 0, b is 1, c is 0, and d is 0. In one embodiment, the initial catalyst composition comprises a metal phosphate of Formula (II) where a is 0, b is 0, c is 1, and d is 0. In one embodiment, the initial catalyst composition comprises a metal phosphate of Formula (II) where a is 0, b is 0, c is 0, and d is 1.

In one embodiment, the initial catalyst composition comprises a metal phosphate of Formula (II) wherein a is any number between 0 and 1 inclusive; b is any number between 0 and 1 inclusive; c is 0; and d is 0. In one embodiment, the initial catalyst composition comprises a metal phosphate of Formula (II) wherein a is any number between 0 and 1 inclusive; b is 0; c is any number between 0 and 1 inclusive; and d is 0. In one embodiment, the initial catalyst composition comprises a metal phosphate of Formula (II) wherein a is any number between 0 and 1 inclusive; b is 0; c is 0; and d is any number between 0 and 1 inclusive. In one embodiment, the initial catalyst composition comprises a metal phosphate of Formula (II) wherein a is 0; b is any number between 0 and 1 inclusive; c is any number between 0 and 1 inclusive; and d is 0. In one embodiment, the initial catalyst composition comprises a metal phosphate of Formula (II) a is 0; b is any number between 0 and 1 inclusive; c is 0; and d is any number between 0 and 1 inclusive. In one embodiment, the initial catalyst composition comprises a metal phosphate of Formula (II) is wherein a is 0; b is 0; c is any number between 0 and 1 inclusive; and d is any number between 0 and 1 inclusive.

The initial catalyst composition may optionally further comprise at least one metal or metal ion selected from the lanthanides, the alkali metals, and the transition metals. In one embodiment, the initial catalyst composition may further comprise at least one metal or metal ion selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb. In one embodiment, the initial catalyst composition may further comprise at least one metal or metal ion selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Ta, W, Re, Ir, Pt, Au, La, Ce, and Yb. In one embodiment, the optional metal(s) or metal ion(s) may be present in an amount less than about 50 mole percent of the total metals $[(M_w+M'_x+M''_y+M'''_z]$ or $[(M_m+M'_n+M''_p+M'''_q]$. In one embodiment, the optional metal(s) or metal ion(s) may be present in an amount less than about 30 mole percent of the total metals $[M_w+M'_x+M''_y+M'''_z]$ or $[(M_m+M'_n+M''_p+M'''_q]$. In one embodiment, the optional metal(s) or metal ion(s) may be present in an amount less than about 15 mole percent of the total metals $[M_w+M'_x+M''_y+M'''_z]$ or $[(M_m+M'_n+M''_p+M'''_q]$. The optional metal(s) or metal ion(s) may be incorporated into the bulk hydroxyapatite during its synthesis, or may be added to the surface of the initial catalyst composition.

The initial catalyst composition may further comprise at least one anionic additive selected from the group consisting of carbonate, silicate, aluminate, arsenate, vanadate, sulfate, and borate. Other additives may be used so long as the presence of the additive is not deleterious to the catalyst composition or its use in the process. In one embodiment, the additive may be present in an amount less than about 10 mole percent of the total metals $[M_w+M'_x+M''_y+M'''_z]$ or $[M_m+M'_n+M''_p+M'''_q]$. In one embodiment, at least some of the phosphate groups of the hydroxyapatite may be substituted by one or more of these anionic additives, for example by arsenate or vanadate.

Base-treated catalyst compositions derived from a hydroxyapatite of Formula (I) or Formula Op can be obtained as nanocrystalline solids. The particles in the nanocrystalline base-treated catalyst composition can have dimensions which range from about 10 nm to about 50 nm in length in the shortest dimension and about 50 nm to about 500 nm in length in the longest dimension, for example from about 10 nm to about 50 nm in length in the shortest dimension and about 80 nm to about 400 nm in length in the longest dimension. Nanocrystalline catalysts can be advantageous due to their higher surface area which increases the amount of conversion per unit mass of catalyst.

The base-treated catalyst compositions can have surface areas of greater than about 2 meters squared per gram. In one embodiment, the catalyst compositions can have a surface area greater than about 5 meters squared per gram. In one embodiment, the catalyst compositions can have a surface area greater than about 10 meters squared per gram. Higher surface area is generally desirable for catalyst compositions as higher surface area can provide higher catalytic activity on a constant weight basis.

The initial catalyst composition comprising a hydroxyapatite of Formula (III) can be synthesized by the methods described above for a catalyst composition comprising a hydroxyapatite of Formula (I), except that the molar ratio of the divalent metals is selected to satisfy the stoichiometry of the hydroxyapatite of Formula (III).

Preferably, the initial catalyst composition comprising a hydroxyapatite of Formula (I) or Formula (III) is calcined before treatment with base.

The initial catalyst composition is contacted with a base to produce a base-treated catalyst composition useful in the process of producing a reaction product comprising 1-butanol. In one embodiment, the base comprises an aqueous solution of a metal hydroxide $Q(OH)_f$ where f is 1 to 3 inclusive and Q is at least one metal selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb, In one embodiment, Q is at least one metal selected from the group consisting of Li, Na, K, Rb, Cs, Sc, Y, Lu, Ti, V, Cr. Mn, Fe, Co, Ni, Cu, Zn, Zr, Nb, Mo, Ru, Rh, Pd. Ag, Ta, W, Re, Ir, Pt, Au, La, Ce, and Yb. In one embodiment, Q is at least one metal selected from the group consisting of Mg, Ca, Sr, and Ba. The metal hydroxide $Q(OH)_f$ can be obtained commercially or can be generated by adding the corresponding metal oxide to water. The pH of the aqueous solution of the metal hydroxide $Q(OH)_f$ should be greater than about 11, for example greater than about 12, or for example greater than about 12.5. The aqueous solution may contain organic solvents as long as the presence of the organic solvent is not deleterious to the process of treating with a base or to the base-treated catalyst composition.

The base-treated catalyst composition can be isolated by filtration or centrifugation. After isolation, the base-treated catalyst composition can be washed with water. In one embodiment, the base-treated catalyst composition is washed with a total of about 0 to about 20 mL of water per g of solid isolated. In one embodiment, the base-treated catalyst composition is washed with about 0 to about 11 mL of water per g of solid. The use of a minimal amount of water, such as less than about 11 mL of water per gram of isolated solid to wash the isolated base-treated catalyst composition can provide improved selectivity to alcohols in a process for producing a reaction product comprising 1-butanol from a reactant comprising ethanol. Optionally, the base-treated catalyst can be dried to remove water.

Preparation of the catalyst composition for use in a process to produce 1-butanol can further include pelletizing the solid base-treated catalyst composition, crushing and sieving the material, and optionally calcining the material at a temperature from about 400 to 800° C., preferably from 500 to 700° C., for a time of about 1 to 24 h, preferably 2 to 10 h in an oven in air.

Contacting the initial catalyst composition with base may be performed in a stirred, or otherwise agitated, batch reactor. The base treatment may be done in air or under an inert atmosphere, such as nitrogen or argon. Optionally, the amount of carbon dioxide present is minimized to reduce its reaction with the base.

Contacting the initial catalyst composition with base is carried out under suitable treatment conditions including a treatment temperature of about 30° C. to about 300° C. In another embodiment, contacting the initial catalyst composition with base is carried out at a temperature of about 25° C. to about 300° C., for example about 30° C. to about 200° C. In another embodiment, contacting the initial catalyst composition with base is carried out at a temperature of about 50° C. to about 200° C.

Contacting the initial catalyst composition with base is carried out for a treatment time of about 1 minute to about 24 hours. Longer periods of base treatment, such as several days, are possible, however a shorter period of time may be preferable for practical, economic reasons. In one embodiment, contacting the initial catalyst composition with base is carried out for a treatment time of about 1 minute to about 18 hours.

In one embodiment, contacting the initial catalyst composition with base may be performed at a relatively high temperature for a relatively short period of time, for example at about 150° C. to about 300° C. for about 1 minute to about 12 hours. In another embodiment, contacting the initial catalyst composition with base may be performed at a lower temperature for a relatively long period of time, for example from about 30° C. to about 150° C. for about 1 to about 48 hours. In one embodiment, contacting the initial catalyst composition with base at about 100° C. is carried out for a treatment time of about 45 minutes to about 90 minutes. Other temperature and treatment time combinations intermediate to these may also be used.

For the process of contacting the initial catalyst composition with base, the temperature, treatment time, pH, metal hydroxide used, initial catalyst composition, and particle size of the initial catalyst composition are related; thus these variables may be adjusted as necessary for each type of initial catalyst composition to optimize the base treatment processes described herein.

Process for Treating Initial Catalyst Composition with Base:

In one embodiment of the invention, a process for contacting an initial catalyst composition comprising a hydroxyapatite of Formula (I) with a base to produce a base-treated catalyst composition is provided. The process comprises contacting an initial catalyst composition comprising a hydroxyapatite of Formula (I) with a base at a temperature from about 30° C. to about 300° C. and for a time of about 1 minute to about 24 hours to produce a base-treated catalyst composition.

In another embodiment of the invention, a process for contacting an initial catalyst composition comprising a hydroxyapatite of Formula (III) with a base to produce a base-treated catalyst composition is provided. The process comprises contacting an initial catalyst composition comprising a hydroxyapatite of Formula (III) with a base at a temperature from about 30° C. to about 300° C. and for a time of about 1 minute to about 24 hours to produce a base-treated catalyst composition.

The initial catalyst composition of either embodiment can be obtained as described above herein, and can further comprise a metal phosphate; at least one metal or metal on selected from the lanthanides, the alkali metals, and the transition metals; at least one additive selected from the group consisting of carbonate, silicate, aluminate, arsenate, vanadate, sulfate, and borate; as described above herein. The base can be as described above herein. The method of contacting the initial catalyst composition and the base can be as described above herein. The process may further comprise the step of washing the base-treated catalyst composition with a minimal amount of water. The washing step may be done at ambient temperature.

Another embodiment of the invention provides a composition comprising a base-treated catalyst derived from a hydroxyapatite of the Formula $(M_w M'_x M''_y M'''_z)_5 (PO_4)_3 (OH)$ wherein M is Mg; M' is Ca; M" is Sr; M''' is Ba; w is any number between 0 and 1 inclusive; x is any number from 0 to less than 0.5; y is any number between 0 and 1 inclusive; z is any number between 0 and 1 inclusive; and w+x+y+z=1; wherein the composition is obtained by the process of contacting an initial catalyst composition comprising a hydroxyapatite of Formula (I) with base as described above herein.

Another embodiment of the invention provides a composition comprising a base-treated catalyst derived from a hydroxyapatite of the Formula $(M_m M'_n M''_p M'''_q)_5 (PO_4)_3 (OH)$ wherein M is Mg; M' is Ca; M" is Sr; M''' is Ba; m is any number between 0 and 1 inclusive; n is any number between 0 and 1 inclusive; p is any number between 0 and 1 inclusive; q is any number between 0 and 1 inclusive; and m+n+p+q=1; wherein the composition is obtained by the process of contacting an initial catalyst composition comprising a hydroxyapatite of Formula (III) with base as described above herein.

Process to Produce a Reaction Product Comprising 1-Butanol:

In one embodiment of the invention, a process is provided in which a gas phase reactant stream comprising ethanol is contacted with a catalyst composition as described herein at a temperature and pressure sufficient to produce a reaction product comprising butanol. The butanol is predominantly 1-butanol. The gas phase reactant stream may be anhydrous, for example containing less than about 0.1 weight percent water, or may contain some water, for example the amount of water present in an ethanol/water azeotrope (96.4% ethanol/3.6% water at atmospheric pressure). The gas phase reactant stream may further comprise other alcohols, such as methanol, other butanol isomers, higher alcohols, and mixtures thereof. Optionally, the gas phase reactant stream may contain an inert gas such as nitrogen, carbon dioxide, or a mixture thereof. The reaction product further comprises water and unreacted ethanol, if ethanol conversion is less than complete. The reaction product may further comprise alcohols containing more than four carbon atoms and other organic species such as alkenes, alkanes, and ethers. Suitable temperatures for the catalytic conversion of a reactant comprising ethanol to a reaction product comprising 1-butanol are in the range of about 150° C. to about 500° C., for example about 200° C. to about 500° C. Suitable pressures are from about 0.1 MPa to about 20.7 MPa, Suitable contact times on the catalyst can range from about 0.25 seconds to about 25 seconds.

The reactant stream comprising ethanol can be obtained from any convenient source. For example, ethanol may be obtained synthetically by direct catalytic hydration of ethylene, indirect hydration of ethylene, conversion of synthesis gas (carbon monoxide and hydrogen), homologation of methanol, carbonylation of methanol and methyl acetate as is known in the art. The reactant stream comprising ethanol may also be obtained by fermentation. For example, ethanol may be produced fermentatively by the yeast *Saccharomyces cerevisiae* or the bacterium *Zymomonas mobilis* using sugars, optionally obtained from cellulosic materials as the carbon and energy source for growth. The result of the fermentation is a fermentation broth, which is then refined to produce a stream of aqueous ethanol. The refining process may comprise at least one distillation column by which an overhead stream comprising an azeotrope of ethanol and water is produced, and whereby the removal of solids, such as cell biomass, unconsumed complex sugars, and precipitated salts or proteins, from the fermentation broth is effected. Once the ethanol-water azeotrope has been distilled off, the ethanol-water azeotrope can be used as the reactant stream for the present invention, or one or more drying procedures can be performed to reduce the amount of water in the overhead stream. While many drying methods are known, generally the wet ethanol stream is passed over a desiccant, such as molecular sieves, until the desired amount of water has been removed.

In another embodiment, a process is provided in which a gas-phase reactant stream comprising a $C_2$-$C_6$ primary or secondary alcohol having a methylene group at the α-position is contacted with a catalyst composition at a temperature and pressure sufficient to produce a reaction product comprising Guerbet alcohol products. Examples of such primary or secondary alcohols include 1-propanol, 1-butanol, 1-pentanol, and 2-methyl-1-butanol. Examples of Guerbet alcohol products which may be produced from these alcohols include ethyl butanol, 1-hexanol, 1-octanol, 2-methylpentanol, 2-ethylhexanol, 2-propylheptanol, and 2,4-dimethylpentanol.

The catalyst compositions useful in the process to produce a reaction product comprising 1-butanol or another Guerbet alcohol can be catalyst compositions comprising a hydroxyapatite of Formula (I) or base-treated catalyst compositions obtained by treating an initial catalyst composition comprising a hydroxyapatite of Formula (I) or Formula (III) with a base, as described above herein. The catalyst compositions may be prepared as described above herein. The catalyst compositions may be used in the form of powders, granules, spheres, pellets, or other particulate forms. Selection of an optimal average particle size for the catalyst composition will depend upon such process parameters as reactor residence time and desired reactor flow rates.

The catalytic conversion of ethanol to the reaction product can be run in either batch or continuous mode as described, for example, in H. Scott Fogler, (*Elements of Chemical Reaction Engineering*, 2$^{nd}$ Edition, (1992) Prentice-Hall Inc, CA). Suitable reactors include fixed-bed, adiabatic, fluid-bed, transport bed, and moving bed.

The catalyst composition may be treated with nitrogen or air at elevated temperatures prior to its use. One protocol that has been found to be effective is described in more detail in Example 1, below. If the catalyst composition comprises at least one transition metal, the catalyst composition may be treated with hydrogen at elevated temperatures prior to its use. If catalyst treatment is desired, the catalyst may be treated in situ in the reactor or ex situ and then introduced into the reactor.

During the course of the reaction, the catalyst may become fouled, and, therefore, it may be necessary to regenerate the catalyst. Preferred methods of catalyst regeneration include, contacting the catalyst composition with a gas such as, but not limited to, air, steam, hydrogen, nitrogen or combinations thereof, at an elevated temperature, although care must be taken not to use a temperature that is so high that the regeneration results in a loss of surface area or other unwanted effects. If catalyst regeneration is desired, the catalyst may be regenerated in situ in the reactor or ex situ and then introduced into the reactor.

One skilled in the art will know that conditions, such as temperature, pressure, catalyst composition, reactor configuration and contact time can affect the reaction kinetics, product yield and product selectivity. Standard experimentation can be used to optimize the yield of 1-butanol from the reaction.

1-Butanol can be separated from the reaction product by known chemical engineering methods, including distillation. Other specific chemicals (or combinations of chemicals) also can be removed from the reaction product using known chemical engineering methods. The specific methods will be dependent on the nature of the reaction product, which, in turn, is dependent on the specific catalyst used and the reaction conditions, particularly the extent of ethanol conversion.

Advantages of the Present Methods:

The catalyst compositions disclosed herein are useful in a process for producing 1-butanol from a reactant comprising ethanol. The catalyst compositions are also useful as initial catalyst compositions which, when contacted with a base as disclosed herein, can provide base-treated catalyst compositions which are also useful in a process for producing 1-butanol from a reactant comprising ethanol and which are expected to provide better performance. The catalyst compositions, and the processes in which they can be used, offer long catalyst lifetime, high selectivity to butanol, and low production of alkenes, alkanes, and diethyl ether.

The processes to produce a reaction product comprising 1-butanol disclosed herein, the catalyst compositions disclosed herein, and the 1-butanol produced by the processes disclosed herein, may be used in a process for making a dialkyl ether composition comprising two or more ethers, as disclosed for example in published patent application WO2009/064828. Such dialkyl ether compositions are useful as a fuel additive.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

The following materials were used in the examples. All commercial reagents were used as received. Ethanol (99.5%), toluene, strontium acetate (99.99%), calcium acetate hydrate (99%), strontium hydroxide (95%), phosphoric acid (99.99%), and barium hydroxide octahydrate (>98%) were obtained from Sigma Aldrich (Milwaukee, Wis.). Barium acetate (99.9%) was obtained from J. T. Baker Chemical Co. (Phillipsburg, N.J.). Toluene from was deoxygenated and dried before use. Ammonium hydroxide (>99%) was obtained from EMD Chemicals, Gibbstown, N.J. The compound bis($\eta^2$, $\eta^2$-1,5-cyclooctadiene)nickel(0) was obtained from Strem Chemicals, Inc. (Newburyport, Mass.).

Electron Spectroscopy for Chemical Analysis (ESCA) was performed using a Quantera SXM (Scanning X-ray Photoelectron Spectroscopy Microprobe) (ULVAC-PHI, Inc.) using the following X-ray settings: 100 μm, 100 W, 17.5 kV, monochromatic Aluminum X-rays. An analysis area of 1350 μm×200 μm was examined. High resolution detail spectral acquisition was achieved using 55 eV pass energy with a 0.2 eV step size.

Powder X-ray diffraction was used for the identification of crystalline phases. Data were obtained with a Philips X'PERT automated powder diffractometer, Model 3040. The diffractometer was equipped with automatic variable anti-scatter and divergence slits, X'Celerator RTMS detector, and Ni filter. The radiation was CuKα (45 kV, 40 mA). Data were collected at room temperature from 4 to 60 degrees 2-theta; using a continuous scan with an equivalent step size of 0.02 deg; and a count time of 80 seconds per step in theta-theta geometry. The sample was ground with an agate mortar and pestle and smeared on an amorphous silicon sample holder. A few drops of collodion were applied to secure the powder sample on the holder, MDI/Jade software was used with the International Committee for Diffraction Data database for phase identification.

Elemental analyses were performed by inductively coupled atomic emission spectroscopy (ICP-AES) using a Perkin Elmer, Model=Optima 5300 instrument used in radial view mode. Analyses were also done on an ELEMENT-2 High Resolution Inductively Coupled Plasma Mass Spectrometer (HR-ICP-MS) manufactured by Thermo Scientific, Inc., and on an Agilent 7500ce ICP-MS.

A Tecnai F-20 Scanning Transmission Electron Microscope (TEM) equipped with a field-emitting electron source was used for the structural and compositional identification of the catalysts. The microscope was operated at an accelerating voltage of 200 kV. The microscope was also equipped with an Oxford Instruments INCA x-sight energy dispersive spectroscopy (EDS) system to identify elements as light as Boron. The EDS system had a Li-doped Si detector and an ATW ultra-thin window. Samples were prepared by dry-dusting them onto holey-carbon coated copper TEM grids (3 mm diameter) without the use of any liquid dispersing aids. Images were acquired using a cold CCD camera mounted on the bottom of the TEM column.

BET surface area was determined using nitrogen adsorption/desorption measurements performed at 77.3° K. on a Micromeritics, Inc. ASAP model 2400/2405 porosimeter. Samples were degassed at 150° C. overnight prior to data collection. Surface area measurements utilized a five-point adsorption isotherm collected from 0.05 to 0.20 p/p$_0$ and analyzed via the BET method.

In the Tables, "EtOH" means ethanol, "Cony." means conversion, "BuOH" means 1-butanol, and "Sel." means selectivity. "Low Boilers" is the sum of the lowest boiling major components of the product stream: ethylene, butenes, 1,3butadiene, acetaldehyde, ethyl ether, hexadienes, butanal and 3-methylene cyclopentene, Ethanol conversion (%) was calculated as follows: [(1-carbon moles of unreacted ethanol)/carbon moles of total outlet gases] times 100, Total BuOH Selectivity (%) was calculated as follows: (carbon moles of 1-BuOH product/carbon moles of ethanol reacted) times 100. Total Alcohol Selectivity (%) was calculated as follows: (carbon moles of all alcohol products/carbon moles of ethanol reacted) times 100. Total Low Boiler Selectivity (%) was calculated as follows: (carbon moles of all low boiling products (as defined above)/carbon moles of ethanol reacted) times 100.

Example 1

Synthesis of Nanocrystalline $Sr_{10}(PO_4)_6(OH)_2$, Base Treatment with $Sr(OH)_2$, and Use of the Base-Treated Catalyst Composition to Produce a Reaction Product Comprising 1-Butanol This Example illustrates the use of a base-treated catalyst composition comprising a strontium hydroxyapatite to produce a product comprising 1-butanol, and a process for making the base-treated catalyst.

A three-necked round-bottomed flask equipped with a pH probe and two inlets for syringe pump tubing was charged with 28.12 g of strontium acetate dissolved in 250.0 mL of deionized water. To this was added via syringe pump 15.58 mL of a 5.24 M solution of phosphoric acid at a rate of 1.039 mL/min. Simultaneously, a concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously during addition, and for 2 h following completion of addition. The former procedures were done under conditions of ambient room temperature.

The white precipitate that formed was isolated by filtration, was washed twice with 100 mL portions of deionized water, and was dried in a vacuum oven overnight at 100° C. Yield of dry product, the initial catalyst composition, was 19.97 g. X-ray powder diffraction of this product showed the presence of a crystalline compound identified as primarily $Sr_{10}(PO_4)_6(OH)_2$. BET Surface Area: 68.8 m$^2$/g. TEM pictures showed the product was primarily $Sr_{10}(PO_4)_6(OH)_2$ rod-like nanocrystals with dimensions of from 10 to 40 nm along the small dimension to 50-300 nm in length. The material was calcined at 600° C. for 8 h in an oven.

To a 500 mL round-bottomed borosilicate flask was charged 7.40 g of the calcined initial catalyst composition, and 78.0 mL of a saturated solution of strontium hydroxide (1.77 g/mL $Sr(OH)_2$). This was refluxed under nitrogen for one hour. After cooling the base-treated product was isolated by filtration, washed twice with 39 mL of portions of distilled water, and then dried in a vacuum oven at 100° C. overnight yielding 7.91 g of base-treated catalyst composition as product. X-ray powder diffraction of this product showed the presence of a crystalline compound identified as primarily $Sr_{10}(PO_4)_6(OH)_2$. BET Surface Area: 42.4 m$^2$/g. TEM pictures showed the base-treated product was primarily $Sr_{10}(PO_4)_6(OH)_2$ rod-like nanocrystals with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

The calcined, base-treated catalyst composition was evaluated according to the following procedure. Approximately 2.7 grams of the catalyst composition was loaded on a stainless steel mesh support within a 18 inch×½ inch (45.7 cm×1.3 cm) outside diameter (o.d.) type 316 stainless steel tube reactor with inlets for gas and liquid feeds. The catalyst composition was then pre-conditioned in situ in the reactor by flowing nitrogen gas at 15 mL/min, initially at room temperature, raising the temperature to 400° C. and introducing the ethanol to generate reaction data. At reaction temperature nitrogen flow was set at 6 mL/min and ethanol flow at 4.0 mL/h. The gaseous product stream was kept at 215° C. and fed directly to an Agilent™ 6890 GC equipped with flame ionization and mass selective detectors. Results are shown in Table 1.

TABLE 1

Ethanol Conversion and Product Selectivity Data for Example 1

| Elapsed Time (hrs) | EtOH Conv. (%) | BuOH Sel. (%) | Low Boilers Sel. (%) | Total Alcohol Sel. (%) |
|---|---|---|---|---|
| 0.5 | 39.6 | 53.6 | 15.9 | 74.5 |
| 1.2 | 32.8 | 56.6 | 17.3 | 74.8 |
| 1.8 | 32.9 | 56.8 | 17.6 | 74.9 |
| 3.9 | 32.3 | 57.2 | 17.4 | 75.2 |
| 5.2 | 32.5 | 57.5 | 17.0 | 75.7 |
| 8.9 | 32.4 | 58.1 | 16.7 | 76.1 |
| 12.0 | 32.3 | 58.4 | 16.5 | 76.4 |
| 18.2 | 31.7 | 58.4 | 16.7 | 76.2 |
| 21.2 | 31.9 | 58.4 | 16.5 | 76.4 |

Example 2

Synthesis of Nanocrystalline $Sr_{10}(PO_4)_6(OH)_2$, Base Treatment with $Sr(OH)_2$, and Use of the Base-Treated Catalyst Composition to Produce a Reaction Product Comprising 1-Butanol This Example illustrates the ethanol conversion and selectivity to various reaction products obtained with a base-treated catalyst composition comprising a strontium hydroxyapatite and calcined at various temperatures for various lengths of time.

The catalyst precursor $Sr_{10}(PO_4)_6(OH)_2$ was prepared according to a procedure similar to that of Example 1. Before base treatment, samples of the catalyst precursor were subjected to different calcining temperatures and times. The various calcined samples were then treated with $Sr(OH)_2$ under the conditions described in Example 1 to obtain samples of base-treated catalyst compositions. Catalyst composition preparation and testing were accomplished as described in Example 1 under the same conditions as in Example 1. The results of the testing are shown in Table 2; the data was taken after approximately 2 h of flow when product output from the catalyst composition had stabilized. From this data, the most preferred conditions for calcining the catalyst precursor were determined to be 600° C.+/−50° C. for a time of about 8 h to about 24 h. These conditions were a compromise between obtaining the highest surface area possible for the catalyst composition while maintaining the lowest selectivity to low boilers during production of a reaction product comprising 1-BuOH.

TABLE 2

Results for Different Catalyst Precursor Calcine Times and Temperatures for Example 2.

| Calcine Temperature (° C.) | Calcine Time (h) | BET Surface Area (m²/g) | EtOH Conv. (%) | BuOH Sel. (%) | Low Boilers Sel. (%) | Total Alcohol Sel. (%) |
|---|---|---|---|---|---|---|
| 450 | 8 | 57.5 | 34.1 | 49.3 | 25.2 | 66.4 |
| 450 | 15 | 53.4 | 35.2 | 52.1 | 20.5 | 71.1 |
| 550 | 8 | 43.2 | 36.6 | 44.8 | 31.5 | 59.8 |
| 550 | 15 | 43.0 | 36.8 | 49.8 | 21.5 | 69.2 |
| 600 | 8 | 28.8 | 36.5 | 55.4 | 14.4 | 75.3 |
| 600 | 15 | 35.0 | 42.5 | 48.0 | 14.8 | 70.3 |
| 600 | 30 | 33.9 | 33.7 | 56.0 | 14.9 | 75.9 |
| 650 | 15 | 11.9 | 24.1 | 52.0 | 17.0 | 70.2 |
| 700 | 15 | 14.2 | 19.1 | 36.5 | 30.2 | 54.2 |

Example 3

Synthesis of Nanocrystalline $Sr_{10}(PO_4)_6(OH)_2$, Base Treatment with $Ba(OH)_2$, and Use of the Base-Treated Catalyst Composition to Produce a Reaction Product Comprising 1-Butanol This example demonstrates the use of barium hydroxide as a suitable base for generating a catalyst composition.

The catalyst precursor $Sr_{10}(PO_4)_6(OH)_2$ was prepared according to a procedure similar to that in Example 1, and calcined at 600° C. for 8 h. For treatment with base, 5.0 g of the calcined material was then placed into a PFA Teflon® round-bottomed flask with 52.7 mL of a solution of $Ba(OH)_2$ (4.59 g of barium hydroxide octahydrate in 100 mL of deionized water) that was stored in a polystyrene bottle. This was stirred at 100° C. under an atmosphere of nitrogen for one hour. After cooling to room temperature, the product was isolated by filtration. It was then dried in a vacuum oven at 100° C. overnight yielding 5.23 g of solid. Catalyst composition preparation and testing was done as described in Example 1.

TABLE 3

Ethanol Conversion and Product Selectivity Data for Example 3.

| Elapsed Time (hrs) | EtOH Conv. (%) | BuOH Sel. (%) | Low Boilers Sel. (%) | Total Alcohol Sel. (%) |
|---|---|---|---|---|
| 0.0 | 29.23 | 54.54 | 12.62 | 70.99 |
| 1.4 | 25.97 | 59.33 | 13.47 | 74.68 |
| 2.7 | 24.84 | 58.85 | 12.79 | 75.48 |
| 4.0 | 25.67 | 58.91 | 12.64 | 75.82 |
| 5.4 | 25.66 | 60.70 | 13.48 | 76.63 |

Example 4

Synthesis of Nanocrystalline $Ca_2Sr_8(PO_4)_6(OH)_2$ and its Use to Produce a Reaction Product Comprising 1-Butanol This Example illustrates the selectivity for a product comprising 1-butanol using a catalyst composition comprising a strontium- and calcium-containing hydroxyapatite that has not been base-treated.

A three-necked round-bottomed flask equipped with a pH probe and two addition funnels was charged with 22.496 g of strontium acetate and 4.838 g of calcium acetate dissolved in 250.0 mL of deionized water. To this was added dropwise, via an addition funnel, 9.412 g of 85% phosphoric acid diluted with 10 mL of deionized water; simultaneously, 75.0 mL of a concentrated ammonium hydroxide solution (14.5 M) was added via the other addition funnel maintaining a pH of >10 in the round-bottomed flask during the addition of reagents. The mixture was stirred vigorously during addition, and for 2 h following completion of addition.

The white precipitate that formed was isolated by filtration, washed twice with 100 mL portions of deionized water, and dried in a vacuum oven overnight at 100° C. Yield of dry product, the catalyst composition, was 18.65 g. X-ray powder diffraction of this product showed the presence of a crystalline compound identified as primarily $Sr_8Ca_2(PO_4)_6(OH)_2$. BET Surface Area: 50.1 m$^2$/g. TEM pictures showed the product was primarily $Sr_8Ca_2(PO_4)_6(OH)_2$ rod-like nanocrystals with dimensions of from 10 to 40 nm along the small dimension to 50-300 nm in length.

The catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

The calcined catalyst composition was evaluated using the procedure of Example 1 but with 2.36 grams of catalyst composition. The results are shown in Table 4.

TABLE 4

Ethanol Conversion and Product Selectivity Data for Example 4.

| Elapsed Time (Hours) | EtOH Conv. (%) | BuOH Sel. (%) | Low Boilers Sel. (%) | Total Alcohol Sel. (%) |
|---|---|---|---|---|
| 0.5 | 21.8 | 5.1 | 88.0 | 6.2 |
| 1.3 | 21.3 | 4.7 | 90.6 | 5.8 |
| 1.9 | 21.4 | 4.6 | 91.8 | 5.5 |
| 2.6 | 21.7 | 4.3 | 92.5 | 5.2 |
| 4.0 | 21.7 | 4.2 | 92.8 | 5.1 |

Example 5

Synthesis of Nanocrystalline $Ca_2Sr_8(PO_4)_6(OH)_2$, Base Treatment with $Sr(OH)_2$ to Produce a Base-Treated Catalyst Composition (Washed with Two Volumes of Water), and Use of the Base-Treated Catalyst Composition to Produce a Reaction Product Comprising 1-Butanol This Example illustrates the use of a base-treated catalyst composition comprising a strontium- and calcium-hydroxyapatite to produce a product comprising 1-butanol, and a process for making the base-treated catalyst composition. Together with Examples 8 and 9, this illustrates the improved selectivity to a product comprising 1-butanol using fewer or no washings of the isolated base-treated catalyst composition.

A three-necked round-bottomed flask equipped with a pH probe and two addition funnels was charged with 22.498 g of strontium acetate and 4.838 g of calcium acetate dissolved in 250.0 mL of deionized water. To this was added dropwise, via an addition funnel, 9.412 g of 85% phosphoric acid diluted with 10 mL of deionized water; simultaneously, 75.0 mL of a concentrated ammonium hydroxide solution (14.5 M) was added via the other addition funnel maintaining a pH of >10 in the round bottomed flask during the addition of reagents. The mixture was stirred vigorously during addition, and for 2 h following completion of addition.

The white precipitate that formed was isolated by filtration, washed twice with 100 mL portions of deionized water, and dried in a vacuum oven overnight at 100° C. Yield of dry product, the initial catalyst composition, was 18.02 g. The X-ray powder diffraction pattern for this material indicated the presence of a phase of approximate formula $Sr_8Ca_2(PO_4)_6(OH)_2$ containing small amounts of $Sr_{2.4}Ca_{0.6}(PO_4)_2$. The BET Surface Area was 51.8 m$^2$/g. ESCA analysis of this product showed the following atomic concentrations (atom %): C, 3.1; O, 59.6; Si, not detectable; P, 13.8; Ca, 3.6; Sr, 19.9. TEM pictures showed this product was primarily $Sr_8Ca_2(PO_4)_6(OH)_2$ rod-like nanoparticles with dimensions of from 10 to 40 nm along the small dimension to 50-300 nm in length. The material was calcined at 600° C. for 8 h in an oven.

To a 500 mL round-bottomed borosilicate flask was charged 9.45 g of the calcined initial catalyst composition, and 100.0 mL of a saturated solution of strontium hydroxide (1.77 g/mL $Sr(OH)_2$). This was refluxed under nitrogen for one hour. After cooling the base-treated product was isolated by filtration and washed twice with 50 mL of portions of deionized water. The wash volume (mL) per gram of catalyst composition was about 10.6, making the catalyst composition minimally washed. The washed catalyst composition was then dried in a vacuum oven at 100° C. overnight yielding 9.55 g of product, the base-treated catalyst composition. The X-ray powder diffraction pattern for this material indicated the presence of a crystalline phase of approximate formula $Sr_8Ca_2(PO4)_6(OH)_2$ containing small amounts of a crystalline phase of approximate formula $Sr_{2.4}Ca_{0.6}(PO_4)_2$. The BET Surface Area was 35.8 m$^2$/g. TEM pictures showed this product was primarily, $Sr_8Ca_2(PO_4)_6(OH)_2$ rod-like nanoparticles with dimensions of from 10 to 40 nm along the small dimension to 50-300 nm in length. ESCA analysis of this product showed the following atomic concentrations (atom %): C, 3.5; O, 57.9; Si, 0.2; P, 12.5; Ca, 3.8; Sr, 22.1. FIG. 1 displays the TEM picture of this catalyst illustrating the typical catalyst particle size and shape. FIG. 2 is a magnified view of one catalyst particle showing the crystalline nature of the catalyst particles. FIG. 3 is the EDS spectrum of the particle shown in FIG. 2 illustrating the presence of strontium and calcium ions throughout the nanocrystal.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence; room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allowed to cool to room temperature.

The calcined base-treated catalyst composition was evaluated using the procedure of Example 1 but with 2.55 grams of catalyst composition. The results are shown in Table 5.

TABLE 5

Ethanol Conversion and Product Selectivity Data for Example 5.

| Elapsed Time (hrs) | EtOH Conv. (%) | BuOH Sel. (%) | Low Boilers Sel. (%) | Total Alcohol Sel. (%) |
|---|---|---|---|---|
| 0.7 | 53.1 | 39.0 | 14.2 | 65.6 |
| 1.3 | 51.5 | 37.4 | 12.5 | 63.4 |
| 5.0 | 41.9 | 46.9 | 14.6 | 70.0 |
| 8.1 | 40.9 | 48.4 | 14.6 | 70.9 |
| 17.2 | 40.9 | 49.3 | 14.6 | 71.8 |
| 21.0 | 41.9 | 47.7 | 14.1 | 71.4 |
| 22.5 | 42.5 | 47.9 | 13.9 | 71.3 |

Example 6

Synthesis of Nanocrystalline $Ca_2Sr_8(PO_4)_6(OH)_2$, Base Treatment with $Sr(OH)_2$, and Use of the Base-Treated Catalyst Composition to Produce a Reaction Product Comprising 1-Butanol This Example illustrates the use of a base-treated catalyst composition comprising a strontium- and calcium-hydroxyapatite to produce a product comprising 1-butanol, and a process for making the base-treated catalyst composition.

A three-necked round-bottomed flask equipped with a pH probe and two inlets for syringe pump tubing was charged with 22.496 g of strontium acetate and 4.838 g of calcium acetate dissolved in 250.0 mL of deionized water. To this was added via syringe pump 15.58 mL of a 5.24 M solution of phosphoric acid at a rate of 1.039 mL/min. Simultaneously, 75.0 mL of concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously, during addition, and for 2 h following completion of addition. The former procedures were done under ambient room temperature conditions.

The white precipitate that formed was isolated by filtration, washed twice with 100 mL portions of deionized water, and dried in a vacuum oven overnight at 100° C. Yield of dry product, the initial catalyst composition, was 18.50 g. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 54.7 m$^2$/g. TEM pictures showed this product was primarily $Sr_8Ca_2(PO_4)_6(OH)_2$ rod-like nanocrystals with dimensions of from 10 to 40 nm along the small dimension to 50-300 nm in length. The material was calcined at 600° C. for 8 h in an oven.

To a 500 mL round-bottomed borosilicate glass flask was charged 7.40 g of the calcined initial catalyst composition, and 78.0 mL of a saturated solution of strontium hydroxide (1.77 g/mL $Sr(OH)_2$) which was prepared and stored in a borosilicate glass bottle. The reaction mixture was refluxed under nitrogen for one hour. After cooling the base-treated product was isolated by filtration, washed twice with 39 mL of portions of distilled water, and then dried in a vacuum oven at 100° C. overnight yielding 7.89 g of base-treated catalyst composition as product. The X-ray powder diffraction pattern for this material indicated the presence of a crystalline phase of approximate formula $Sr_8Ca_2(PO_4)_6(OH)_2$ containing small amounts of a crystalline phase of approximate formula $Sr_{2.7}Ca_{0.3}(PO_4)_2$. The BET Surface Area was 37.5 m$^2$/g. TEM pictures showed this Product was primarily $Sr_8Ca_2(PO_4)_6(OH)_2$ rod-like nanocrystals with dimensions of from 10 to 40 nm along the small dimension to 50-300 nm in length. ICP Trace metal analysis (in ug/g product): Al, 145; B, 130; Ba, 960; Ca, Major; Cr, 10; Cu, <1; Fe, 18; Mg, 260; Mn, 115; Na, 31; P, Major; Si, 885; Sr, Major; Zn, 7; Zr, 30.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

The calcined base-treated catalyst composition was evaluated using the procedure of Example 1, but with 2.71 grams of catalyst composition. The results are shown in Table 6.

TABLE 6

Ethanol Conversion and Product Selectivity Data for Example 6.

| Elapsed Time (hrs) | EtOH Conv. (%) | BuOH Sel. (%) | Low Boilers Sel. (%) | Total Alcohol Sel. (%) |
|---|---|---|---|---|
| 4.3 | 34.1 | 48.7 | 27.3 | 63.2 |
| 7.4 | 33.3 | 49.7 | 25.0 | 64.9 |
| 10.4 | 33.6 | 50.0 | 25.0 | 65.3 |
| 13.5 | 33.0 | 50.5 | 24.8 | 65.3 |
| 16.5 | 33.3 | 50.3 | 25.1 | 65.2 |
| 18.6 | 33.3 | 50.9 | 25.7 | 65.8 |

Example 7

Synthesis of Nanocrystalline $Ca_2Sr_8(PO_4)_6(OH)_2$, Base Treatment with $Sr(OH)_2$, and Use of the Base-Treated Catalyst Composition to Produce a Reaction Product Comprising 1-Butanol This Example illustrates the use of a base-treated catalyst composition comprising a strontium- and calcium-hydroxyapatite to produce a product comprising 1-butanol, and a process for making the base-treated catalyst composition.

A portion of the 18.50 g of initial catalyst composition described in Example 4 above (not treated with base) was used as the initial catalyst composition for this Example and was calcined at 600° C. for 8 h. To a 500 mL round-bottomed polypropylene flask was charged 7.40 g of the calcined product, and 78.0 mL of a saturated solution of strontium hydroxide (1.77 g/mL $Sr(OH)_2$) which was prepared and stored in a plastic polystyrene bottle to avoid contact with glass. This reaction mixture was refluxed under nitrogen for one hour.

After cooling the base-treated product was isolated by filtration, washed twice with 39 mL of portions of distilled water, and then dried in a vacuum oven at 100° C. overnight yielding 7.76 g of base-treated catalyst composition. The X-ray powder diffraction pattern for this material indicated the presence of a crystalline phase of approximate formula $Sr_8Ca_2(PO_4)_6(OH)_2$ containing small amounts of a crystalline phase of approximate formula $Sr_{2.7}Ca_{0.3}(PO_4)_2$. The BET Surface Area was 37.1 m$^2$ μg. TEM pictures showed this product was primarily $Sr_8Ca_2(PO_4)_6(OH)_2$ rod-like nanocrystals with dimensions of from 10 to 40 nm along the small dimension to 50-300 nm in length. ICP Trace metal analysis (in ug/g product): Al, 135; B, 75; Ba, 990; Ca, Major; Cr, 12; Cu, 1; Fe, 21; Mg, 100; Mn, 115; Na, 67; P, Major; Si, 430; Sr, Major; Zn, 11; Zr, 21.

The base-treated catalyst composition was pelletized in a Specac 1 inch stainless steel pellet the at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

This calcined base-treated catalyst composition was evaluated using the procedure of Example 1, but with 2.71 grams of catalyst composition. The results are shown in Table 7.

TABLE 7

Ethanol Conversion and Product Selectivity Data for Example 7.

| Elapsed Time (hrs) | EtOH Conv. (%) | BuOH Sel. (%) | Low Boilers Sel. (%) | Total Alcohol Sel. (%) |
|---|---|---|---|---|
| 0.5 | 39.0 | 30.2 | 49.4 | 38.7 |
| 1.8 | 30.5 | 24.5 | 63.2 | 29.9 |
| 4.5 | 27.3 | 23.8 | 64.6 | 28.7 |
| 7.9 | 27.0 | 24.2 | 64.3 | 29.1 |
| 9.9 | 26.4 | 24.3 | 64.5 | 29.1 |
| 14.0 | 26.2 | 24.0 | 64.9 | 28.7 |
| 18.1 | 25.8 | 24.0 | 64.1 | 27.6 |

Example 8

Synthesis of Nanocrystalline $Ca_2Sr_8(PO_4)_6(OH)_2$, Base Treatment with $Sr(OH)_2$ to Produce a Base-Treated Catalyst Composition (Washed with One Volume Water), and Use of the Base-Treated Catalyst Composition to Produce a Reaction Product Comprising 1-Butanol This Example illustrates the use of a base-treated catalyst composition comprising a strontium- and calcium-hydroxyapatite to produce a product comprising 1-butanol, and a process for making the base-treated catalyst composition. Together with Examples 5 and 9, this illustrates the improved selectivity to a product comprising 1-butanol using fewer or no washings of the isolated base-treated catalyst composition.

A three-necked round-bottomed flask equipped with a pH probe and two inlets for syringe pump tubing was charged with 22.496 g of strontium acetate and 4.838 g of calcium acetate dissolved in 250.0 mL of deionized water. To this was added via syringe pump 15.58 mL of a 5.24 M solution of phosphoric acid at a rate of 1.039 mL/min. Simultaneously, 75.0 mL of concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously during addition, and for 2 h following completion of addition. The former procedures were done under ambient room temperature conditions.

The white precipitate that formed was isolated by filtration, washed twice with 100 mL portions of deionized water, and dried in a vacuum oven overnight at 100° C. Yield of dry product, the initial catalyst composition, was 18.56 g. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 48.8 m²/g. TEM pictures showed this product was primarily $Sr_8Ca_2(PO_4)_6(OH)_2$ rod-like nanocrystals with dimensions of from 10 to 40 nm along the small dimension to 50-300 nm in length. The material was calcined at 600° C. for 8 h in an oven.

To a 500 mL round-bottomed borosilicate glass flask was charged 5.70 g of the calcined initial catalyst composition, and 60.3 mL of a saturated solution of strontium hydroxide (1.77 g/mL $Sr(OH)_2$) which was prepared and stored in a borosilicate glass bottle. The reaction mixture was refluxed under nitrogen for one hour. After cooling the base-treated product was isolated by filtration and washed once with 39 mL of distilled water. The wash volume (mL) per gram of catalyst composition was about 6.4, making the catalyst composition minimally washed. The washed catalyst composition was then dried in a vacuum oven at 100° C. overnight yielding 6.09 g of base-treated catalyst composition as the product. The X-ray powder diffraction pattern for this material indicated the presence of a phase of approximate formula $Sr_8Ca_2(PO_4)_6(OH)_2$ containing small amounts of $Sr_{2.7}Ca_{03}(PO_4)_2$. The BET Surface Area was 36.8 m²/g. TEM pictures showed this product was primarily $Sr_8Ca_2(PO_4)_6(OH)_2$ rod-like nanocrystals with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

This calcined base-treated catalyst composition was evaluated using the procedure of Example 1, but with 2.45 grams of catalyst composition. The results are shown in Table 8.

TABLE 8

Ethanol Conversion and Product Selectivity Data for Example 8.

| Elapsed Time (hrs) | EtOH Conv. (%) | BuOH Sel. (%) | Low Boilers Sel. (%) | Total Alcohol Sel. (%) |
|---|---|---|---|---|
| 0.5 | 43.8 | 48.3 | 19.2 | 68.6 |
| 2.5 | 36.5 | 52.8 | 19.7 | 70.9 |
| 4.6 | 35.4 | 53.1 | 20.3 | 70.7 |
| 6.6 | 35.0 | 54.0 | 20.1 | 71.4 |
| 10.7 | 33.4 | 53.4 | 19.7 | 71.5 |
| 14.8 | 34.7 | 54.8 | 19.0 | 72.5 |
| 20.5 | 34.5 | 54.6 | 19.5 | 72.2 |

Example 9

Synthesis of Nanocrystalline $Ca_2Sr_8(PO_4)_6(OH)_2$, Base Treatment with $Sr(OH)_2$ to Produce a Base-Treated Catalyst Composition (Not Washed), and Use of the Base-Treated Catalyst Composition to Produce a Reaction Product Comprising 1-Butanol This Example illustrates the use of a base-treated catalyst composition comprising a strontium- and calcium-hydroxyapatite to produce a product comprising 1-butanol, and a process for making the base-treated catalyst composition. Together with Examples 5 and 8, this illustrates the improved selectivity to a product comprising 1-butanol using fewer or no washings of the isolated base-treated solid.

A three-necked round-bottomed flask equipped with a pH probe and two inlets for syringe pump tubing was charged with 22.496 g of strontium acetate and 4.838 g of calcium acetate dissolved in 250.0 mL of deionized water. To this was added via syringe pump 15.58 mL of a 5.24 M solution of phosphoric acid at a rate of 1.039 mL/min. Simultaneously, 75.0 mL of concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously during addition, and for 2 h following completion of addition. The former procedures were done under ambient room temperature conditions.

The white precipitate that formed was isolated by filtration, washed twice with 100 mL portions of deionized water, and dried in a vacuum oven overnight at 100° C. Yield of dry product, the initial catalyst composition, was 18.56 g. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 48.8 m²/g. TEM pictures showed this product was primarily $Sr_8Ca_2(PO_4)_6(OH)_2$ rod-like nanocrystals with dimensions of from 10 to 40 nm along the small dimension to 50-300 nm in length. The material was calcined at 600° C. for 8 h in an oven.

To a 500 mL round-bottomed borosilicate glass flask was charged 5.70 g of the calcined initial catalyst composition, and 60.3 mL of a saturated solution of strontium hydroxide (1.77 g/mL $Sr(OH)_2$) which was prepared and stored in a borosilicate glass bottle. The reaction mixture was refluxed under nitrogen for one hour. After cooling the base-treated product was isolated by filtration, and then dried in a vacuum oven at 100° C. overnight yielding 6.08 g of base-treated catalyst composition as the product. The base-treated product was not washed with water after filtration and before drying. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 36.7 m²/g. TEM pictures showed this product was primarily $Sr_8Ca_2(PO_4)_6(OH)_2$ rod-like nanocrystals with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

This calcined base-treated catalyst composition was evaluated using the procedure of Example 1, but with 2.79 grams of catalyst composition. The results are shown in Table 9.

TABLE 9

Ethanol Conversion and Product Selectivity Data for Example 9.

| Elapsed Time (hrs) | EtOH Conv. (%) | BuOH Sel. (%) | Low Boilers Sel. (%) | Total Alcohol Sel. (%) |
| --- | --- | --- | --- | --- |
| 0.7 | 43.1 | 49.2 | 16.9 | 70.7 |
| 2.7 | 40.8 | 50.9 | 17.6 | 71.6 |
| 6.1 | 39.3 | 51.3 | 17.9 | 72.2 |
| 12.2 | 38.9 | 53.1 | 17.8 | 73.1 |
| 16.3 | 38.5 | 52.5 | 18.1 | 72.8 |
| 23.0 | 36.6 | 53.4 | 15.8 | 75.3 |
| 28.4 | 36.0 | 54.8 | 16.4 | 75.3 |
| 36.4 | 36.3 | 54.7 | 16.3 | 75.4 |
| 44.6 | 35.4 | 55.2 | 15.4 | 75.0 |

Example 10

Synthesis of Nanocrystalline $Ca_2Sr_8(PO_4)_6(OH)_2$, Base Treatment with $Sr(OH)_2$ (pH=11.9) to Produce a Base-Treated Catalyst Composition, and Use of the Base-Treated Catalyst Composition to Produce a Reaction Product Comprising 1-Butanol This Example illustrates the use of a base-treated catalyst composition comprising a strontium- and calcium-hydroxyapatite to produce a product comprising 1-butanol, and a process for making the base-treated catalyst composition. Together with Examples 11 and 12, this illustrates the improved selectivity to a product comprising 1-butanol when the base-treatment is done at a pH>12.5 at 100° C. and 60 min.

A three-necked round-bottomed flask equipped with a pH probe and two inlets for syringe pump tubing was charged with 22.496 g of strontium acetate and 4.838 g of calcium acetate dissolved in 250.0 mL of deionized water. To this was added via syringe pump 15.58 mL of a 5.24 M solution of phosphoric acid at a rate of 1.039 mL/min. Simultaneously, 75.0 mL of concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously during addition, and for 2 h following completion of addition. The former procedures were done under ambient room temperature conditions.

The white precipitate that formed was isolated by filtration, was washed twice with 100 mL portions of deionized water, and was dried in a vacuum oven overnight at 100° C. Yield of dry product, the initial catalyst composition, was 18.81 g. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 51.5 m²/g. TEM pictures showed this product was primarily $Sr_8Ca_2(PO_4)_6(OH)_2$ rod-like nanocrystals with dimensions of from 10 to 40 nm along the small dimension to 50-300 nm in length. The material was calcined at 600° C. for 8 h in an oven.

To a 100 mL round-bottomed borosilicate glass flask was charged 5.70 g of the calcined initial catalyst composition and 60.3 mL of a solution of strontium hydroxide (0.110 g/100 mL, pH 11.90) that was stored in a borosilicate glass bottle. The reaction mixture was refluxed under nitrogen for one hour. After cooling the base-treated product was isolated by filtration, and then dried in a vacuum oven at 100° C. overnight yielding 5.57 g of base-treated catalyst composition as product. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 28.0 m²/g. TEM pictures showed this product was primarily $Sr_8Ca_2(PO_4)_6(OH)_2$ rod-like nanocrystals with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved is through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

This calcined base-treated catalyst composition was evaluated using the procedure of Example 1, but with 2.41 grams of catalyst composition. The results are shown in Table 10.

TABLE 10

Ethanol Conversion and Product Selectivity Data for Example 10.

| Elapsed Time (hrs) | EtOH Conv. (%) | BuOH Sel. (%) | Low Boilers Sel. (%) | Total Alcohol Sel. (%) |
|---|---|---|---|---|
| 0.7 | 23.6 | 4.5 | 91.3 | 5.3 |
| 1.3 | 24.1 | 4.3 | 91.8 | 5.1 |
| 2.0 | 24.1 | 4.3 | 91.9 | 5.1 |
| 2.7 | 23.7 | 4.3 | 92.1 | 5.1 |
| 3.4 | 23.5 | 4.2 | 92.3 | 5.0 |

Example 11

Synthesis of Nanocrystalline $Ca_2Sr_8(PO_4)_6(OH)_2$, Base Treatment with $Sr(OH)_2$ (pH=12.5) to Produce a Base-Treated Catalyst Composition, and Use of the Base-Treated Catalyst Composition to Produce a Reaction Product Comprising 1-Butanol This Example illustrates the use of a base-treated catalyst composition comprising a strontium- and calcium-hydroxyapatite to produce a product comprising 1-butanol, and a process for making the base-treated catalyst composition. Together with Examples 10 and 12, this illustrates the improved selectivity to a product comprising 1-butanol when the base-treatment is done at a pH>12.5 at 100° C. and 60 min.

A three-necked round-bottomed flask equipped with a pH probe and two inlets for syringe pump tubing was charged with 22.496 g of strontium acetate and 4.838 g of calcium acetate dissolved in 250.0 mL of deionized water. To this was added via syringe pump 15.58 mL of a 5.24 M solution of phosphoric acid at a rate of 1.039 mL/min. Simultaneously, 75.0 mL of concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously during addition, and for 2 h following completion of addition. The former procedures were done under ambient room temperature conditions.

The white precipitate that formed was isolated by filtration, washed twice with 100 mL portions of deionized water, and dried in a vacuum oven overnight at 100° C. Yield of dry product, the initial catalyst composition, was 18.81 g. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 51.5 m$^2$/g. TEM pictures showed this product was primarily $Sr_8Ca_2(PO_4)_6(OH)_2$ rod-like nanocrystals with dimensions of from 10 to 40 nm along the small dimension to 50-300 nm in length. The material was calcined at 600° C. for 8 h in an oven.

To a 100 mL round-bottomed borosilicate glass flask was charged 5.70 g of the calcined initial catalyst composition and 60.3 mL of a solution of strontium hydroxide (0.442 g/100 mL, pH=12.47) that was stored in a borosilicate glass bottle. The reaction mixture was refluxed under nitrogen for one hour. After cooling the base-treated product was isolated by filtration, and then dried in a vacuum oven at 100° C. overnight yielding 5.70 g of base-treated catalyst composition as product. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 36.2 m$^2$/g. TEM pictures showed this product was primarily $Sr_3Ca_2(PO_4)_6(OH)_2$ rod-like nanocrystals with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

This calcined base-treated catalyst composition was evaluated using the procedure of Example 1, but with 2.61 grams of catalyst composition. The results are shown in Table 11.

TABLE 11

Ethanol Conversion and Product Selectivity Data for Example 11.

| Elapsed Time (hrs) | EtOH Conv. (%) | BuOH Sel. (%) | Low Boilers Sel. (%) | Total Alcohol Sel. (%) |
|---|---|---|---|---|
| 0.0 | 25.3 | 5.8 | 90.6 | 7.0 |
| 2.7 | 24.5 | 4.9 | 92.3 | 5.8 |
| 6.8 | 24.1 | 4.7 | 92.7 | 5.5 |
| 10.9 | 24.0 | 4.8 | 92.7 | 5.6 |
| 14.9 | 24.0 | 4.6 | 92.9 | 5.4 |
| 19.0 | 23.6 | 4.6 | 93.0 | 5.3 |
| 23.1 | 24.1 | 4.4 | 93.1 | 5.2 |

Example 12

Synthesis of Nanocrystalline $Ca_2Sr_8(PO_4)_6(OH)_2$, Base Treatment with $Sr(OH)_2$ (pH=13.0) to Produce a Base-Treated Catalyst Composition, and Use of the Base-Treated Catalyst Composition to Produce a Reaction Product Comprising 1-Butanol This Example illustrates the use of a base-treated catalyst composition comprising a strontium- and calcium-hydroxyapatite to is produce a product comprising 1-butanol, and a process for making the base-treated catalyst composition. Together with Examples 10 and 11, this illustrates the improved selectivity to a product comprising 1-butanol when the base-treatment is done at a pH>12.5 at 100° C. and 60 min, A three-necked round-bottomed flask equipped with a pH probe and two inlets for syringe pump tubing was charged with 22.496 g of strontium acetate and 4.838 g of calcium acetate dissolved in 250.0 mL of deionized water. To this was added via syringe pump 15.58 mL of a 5.24 M solution of phosphoric acid at a rate of 1.039 mL/min. Simultaneously, 75.0 mL of concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously during addition, and for 2 h following completion of addition. The former procedures were done under ambient room temperature conditions.

The white precipitate that formed was isolated by filtration, washed twice with 100 mL portions of deionized water, and dried in a vacuum oven overnight at 100° C. Yield of dry product, the initial catalyst composition, was 18.81 g. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$. The BET Surface Area was 51.5 m²/g. TEM pictures showed this product was primarily $Sr_8Ca_2(PO_4)_6(OH)_2$ rod-like nanocrystals with dimensions of from 10 to 40 nm along the small dimension to 50-300 nm in length. The material was calcined at 600° C. for 8 h in an oven.

To a 100 mL round-bottomed borosilicate glass flask was charged 5.70 g of the initial catalyst composition and 60.3 mL of a solution of strontium hydroxide (1.77 g/100 ml, pH 13.0) that was stored in a borosilicate glass bottle. The reaction mixture was refluxed under nitrogen for one hour. After cooling the base-treated product was isolated by filtration, and then dried in a vacuum oven at 100° C. overnight yielding 5.57 g of base-treated catalyst composition as product. The X-ray powder diffraction pattern for this material indicated the presence of a phase of approximate formula $Sr_8Ca_2(PO_4)_6(OH)_2$ containing small amounts of $Sr_{2.7}Ca_{0.3}(PO_4)_2$.

550° C. at 1° C./min; hold at 550° C. for 8 h. Cool 550° C. to 110° C. at <30° C./min; then allow to cool to room temperature.

This calcined base-treated catalyst composition was evaluated using the procedure of Example 1, but with 2.87 grams of catalyst composition. The results are shown in Table 12.

TABLE 12

Ethanol Conversion and Product Selectivity Data for Example 12.

| Elapsed Time (hrs) | EtOH Conv. (%) | BuOH Sel. (%) | Low Boilers Sel. (%) | Total Alcohol Sel. (%) |
|---|---|---|---|---|
| 0.7 | 65.3 | 29.7 | 16.6 | 58.3 |
| 2.7 | 58.5 | 34.0 | 18.4 | 60.8 |
| 4.1 | 57.3 | 34.5 | 19.8 | 60.1 |
| 12.3 | 53.3 | 39.5 | 20.4 | 64.5 |
| 23.3 | 42.2 | 47.8 | 15.5 | 72.0 |
| 26.1 | 39.7 | 50.5 | 15.7 | 73.2 |
| 31.5 | 36.5 | 52.4 | 16.1 | 73.1 |
| 35.6 | 33.5 | 50.6 | 18.7 | 71.8 |
| 47.9 | 35.5 | 52.4 | 17.0 | 74.2 |
| 54.1 | 33.4 | 53.1 | 17.7 | 73.9 |
| 64.4 | 35.8 | 54.3 | 17.3 | 74.5 |

The following Table 13 summarizes synthesis and evaluation data for Examples 4 through 12 and includes the longest time data point, shown as an approach to a steady state value, for the reactor results.

TABLE 13

Summary of Reactor Data in Examples 4 to 12.

| Example | % Sr[a] | % Ca[a] | pH of Sr(OH)₂ base solution | Glass vs Plastic[b] | Wash Amount[c] | EtOH Conv. (%) | BuOH Sel. (%) | Low Boilers Sel. (%) | Total Alcohol Sel. |
|---|---|---|---|---|---|---|---|---|---|
| 4 | 80% | 20% | 13.0 | Glass | — | 21.7 | 4.2 | 92.8 | 5.1 |
| 5 | 80% | 20% | 13.0 | Glass | 10.6 | 42.5 | 47.9 | 13.9 | 71.3 |
| 6 | 80% | 20% | 13.0 | Glass | 10 | 33.3 | 50.9 | 25.7 | 65.8 |
| 7 | 80% | 20% | 13.0 | Plastic | 10 | 25.8 | 24 | 64.1 | 27.6 |
| 8 | 80% | 20% | 13.0 | Glass | 5 | 34.5 | 54.6 | 19.5 | 72.2 |
| 9 | 80% | 20% | 13.0 | Glass | 0 | 35.4 | 55.2 | 15.4 | 75.0 |
| 10 | 80% | 20% | 11.9 | Glass | 0 | 23.5 | 4.2 | 92.3 | 5.0 |
| 11 | 80% | 20% | 12.5 | Glass | 0 | 24.1 | 4.4 | 93.1 | 5.2 |
| 12 | 80% | 20% | 13.0 | Glass | 0 | 35.8 | 54.3 | 17.3 | 74.5 |

Notes:
[a]% Sr and % Ca refer to the composition, on a molar basis, of the evaluated catalyst composition.
[b]Indicates material of construction for vessel used for preparation of evaluated catalyst composition.
[c]Refers to wash volume (mL) per gram of base-treated catalyst composition The BET Surface Area was 34.0 m²/g. TEM pictures showed this product was primarily $Sr_8Ca_2(PO_4)_6(OH)_2$ rod-like nanocrystals with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./rain rise; hold at 475° C. for 10 min; 475° C. to 525° C. at 5° C./min; hold at 525° C. for 10 min; 525° C. to The catalyst composition evaluation results for Example 4, in which the catalyst composition was not treated with a base, showed similar results as those for Examples 10 and 11, in which the pH of the Sr(OH)₂ base solution during base treatment of the initial catalyst composition was 11.9 or 12.5, respectively. The catalyst composition evaluation results for Example 12, when compared to those for Examples 10 and 11, showed the higher ethanol conversion and total alcohol selectivity obtained with a base-treated catalyst composition where the base treatment used a pH 13.0 solution of strontium hydroxide which had been stored in a borosilicate glass bottle.

Example 13

Synthesis of Nanocrystalline $Ba_{10}(PO_4)_6(OH)_2$, Base Treatment with $Ba(OH)_2$ to Produce a Base-Treated Catalyst Composition, and Use of the Base-Treated Catalyst Composition to Produce a Reaction Product Comprising 1-Butanol This Example illustrates the use of a base-treated catalyst composition comprising a barium hydroxyapatite to produce a product comprising 1-butanol, and a process for making the base-treated catalyst composition.

Barium hydroxide octahydrate (20.0 g) was dissolved in 1800 mL of degassed deionized water and refluxed under nitrogen for one hour. After cooling it was allowed to stand for 24 h. An insoluble precipitate ($BaCO_3$, 2.84 g) was removed by filtration. The filtrate was placed into a three-necked, round-bottomed flask and the solution was heated to 78° C. To this was added dropwise via an addition funnel 27.0 mL of phosphoric acid (0.58 M); the pH of the solution was 12.75 after addition. After 1 hour the stirring was stopped and the reaction was heated to 99° C. for 24 h.

The precipitate was isolated by filtration. This was washed twice with 200 mL of deionized water and dried in a vacuum oven overnight at 100° C. The yield of dry product, the initial catalyst composition, was 5.9 g. The product was calcined at 600° C. for 2 h.

The calcined material was then placed into a round-bottomed flask and 100 mL of a saturated solution of barium hydroxide (3.89 g/100 mL) was added. This was refluxed under nitrogen for 2 h. After cooling, the base-treated product was isolated by filtration and dried in a vacuum oven overnight at 100° C. Yield of base-treated catalyst composition as the product was 6.01 g. The X-ray powder diffraction pattern for this material indicated the presence of a crystalline phase of formula $Ba_{10}(PO_4)_6(OH)_2$ containing small amounts of phases of barium silicate ($BaSiO_3$) and barium hydrogen silicate ($BaH_2SiO_4$). The BET Surface Area was 13.7 m$^2$/g. TEM pictures showed this product was primarily agglomerates of nanocrystals with dimensions of from 20 to 50 nm along the small dimension to 50-400 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° a/min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 10° C. at <30° C./min; then allow to cool to room temperature.

The calcined base-treated catalyst composition was evaluated according to the following procedure.

Approximately 3.54 grams of catalyst composition was loaded on a stainless steel mesh support within a 18 inch×½ inch (45.7 cm×1.3 cm) outside diameter (o.d.) type 316 stainless steel tube reactor with inlets for gas and liquid feeds. The catalyst composition was then pre-conditioned in situ in the reactor by flowing nitrogen gas at 15 mL/min, initially at room temperature, raising the temperature to 350° C. and introducing the ethanol to generate reaction data. At reaction temperature nitrogen flow was set at 15 mL/min and ethanol flow at 4.0 mL/h. The gaseous product stream was kept at 215° C. and fed directly to an Agilent™ 6890 GC equipped with flame ionization and mass selective detectors. Results are shown in Table 14.

TABLE 14

Ethanol Conversion and Product Selectivity Data for Example 13.

| Elapsed Time (hrs) | EtOH Conv. (%) | BuOH Sel. (%) | Low Boilers Sel. (%) | Total Alcohol Sel. (%) |
|---|---|---|---|---|
| 0.0 | 8.8 | 50.6 | 19.0 | 68.7 |
| 0.7 | 6.6 | 44.1 | 24.5 | 63.5 |
| 1.3 | 6.2 | 45.3 | 24.6 | 64.7 |
| 2.0 | 6.2 | 45.1 | 24.3 | 64.5 |
| 2.7 | 6.3 | 45.2 | 24.2 | 64.6 |
| 3.4 | 6.1 | 45.1 | 24.3 | 64.5 |

Example 14

Synthesis of Nanocrystalline $Ca_2Sr_8(PO_4)_6(OH)_2$, Base Treatment with $Sr(OH)_2$ at 25° C. to Produce a Base-Treated Catalyst Composition, and Use of the Base-Treated Catalyst Composition to Produce a Reaction Product Comprising 1-Butanol This Example illustrates the use of a base-treated catalyst composition comprising a strontium- and calcium-hydroxyapatite to produce a product comprising 1-butanol, and together with Example 3 to illustrates the improved selectivity obtained with heating above 25° C. during base-treatment.

A three-necked round-bottomed flask equipped with a pH probe and two addition funnels was charged with 22.498 g of strontium acetate and 4.838 g of calcium acetate dissolved in 250.0 mL of deionized water. To this was added dropwise, via an addition funnel, 9.412 g of 85% phosphoric acid diluted with 10 mL of deionized water; simultaneously, 75.0 mL of a concentrated ammonium hydroxide solution (14.5 M) was added via the other addition funnel maintaining a pH of >10 in the round bottomed flask during the addition of reagents. The mixture was stirred vigorously during addition, and for 2 h following completion of addition.

The white precipitate that formed was isolated by filtration, washed twice with 100 mL portions of deionized water, and dried in a vacuum oven overnight at 100° C. Yield of dry product, the initial catalyst composition, was 18.02 g. The X-ray powder diffraction pattern for this material indicated the presence of a phase of approximate formula $Sr_8Ca_2(PO_4)_6(OH)_2$ containing small amounts of $Sr_{2.4}Ca_{0.6}(PO_4)_2$. The BET Surface Area was 51.8 m$^2$/g. ESCA analysis of this product showed the following atomic concentrations (atom %): C, 3.1; O, 59.6; Si, not detectable; P, 13.8; Ca, 3.6; Sr, 19.9. TEM pictures showed this product was primarily $Sr_8Ca_2(PO_4)_6(OH)_2$ rod-like nanoparticles with dimensions of from 10 to 40 nm along the small dimension to 50-300 nm in length. The material was calcined at 600° C. for 8 h in an oven.

To a 500 mL round-bottomed borosilicate flask was charged 7.40 g of the calcined initial catalyst composition, and 78.0 mL of a saturated solution of strontium hydroxide (1.77 g/mL $Sr(OH)_2$). This was stirred under nitrogen for one hour at 25° C. The product was isolated by filtration and washed twice with 39.0 mL portions of deionized water. The wash volume (mL) per gram of catalyst composition was about 10.6, making the catalyst composition minimally washed. The washed catalyst composition was then dried in a vacuum oven at 100° C. overnight yielding 7.4 g of product, the base-treated catalyst composition. The X-ray powder diffraction pattern for this material indicated the presence of a crystalline phase of approximate formula $Sr_8Ca_2(PO_4)_6(OH)_2$ containing small amounts of a crystalline phase of approximate formula $Sr_{2.4}Ca_{0.6}(PO_4)_2$. The BET Surface Area was 26.4 m²/g. TEM pictures showed this product was primarily $Sr_8Ca_2(PO_4)_6(OH)_2$ rod-like nanoparticles with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allowed to cool to room temperature.

The calcined base-treated catalyst composition was evaluated according to the following procedure.

Approximately 2.47 grams of the catalyst composition was loaded on a stainless steel mesh support within a 18 inch×½ inch (45.7 cm×1.3 cm) outside diameter (o.d.) type 316 stainless steel tube reactor with inlets for gas and liquid feeds. The catalyst composition was then pre-conditioned in situ in the reactor by flowing nitrogen gas at 15 mL/min, initially at room temperature, then raising the temperature to 400° C. and introducing the ethanol to generate reaction data. At reaction temperature nitrogen flow was set at 6 mL/min and ethanol flow at 4.0 mL/h. The gaseous product stream was kept at 215° C. and fed directly to an Agilent™ 6890 GC equipped with flame ionization and mass selective detectors. Results are shown in Table 15.

TABLE 15

Ethanol Conversion and Product Selectivity Data for Example 14.

| Elapsed Time (hrs) | EtOH Conv. (%) | BuOH Sel. (%) | Low Boilers Sel. (%) | Total Alcohol Sel. (%) |
|---|---|---|---|---|
| 0.7 | 23.6 | 4.4 | 91.4 | 5.1 |
| 1.3 | 23.8 | 3.9 | 92.5 | 4.6 |
| 2.0 | 24.8 | 3.8 | 93.0 | 4.4 |
| 3.4 | 24.0 | 3.7 | 93.5 | 4.3 |
| 4.1 | 23.1 | 3.6 | 93.9 | 4.2 |
| 4.7 | 23.2 | 3.5 | 94.2 | 4.1 |

Example 15

Synthesis of Nanocrystalline $Ca_2Sr_8(PO_4)_6(OH)_2$, Base Treatment with $Sr(OH)_2$ to Produce a Base-Treated Catalyst Composition, and Use of the Base-Treated Catalyst Composition to Produce a Reaction Product Comprising 1-Butanol This Example is a demonstration of catalyst lifetime.

A three-necked round-bottomed flask equipped with a pH probe and two addition funnels was charged with 22.496 g of strontium acetate and 4.838 g of calcium acetate dissolved in 250.0 mL of deionized water. To this was added dropwise, via an addition funnel, 9.412 g of 85% phosphoric acid diluted with 10 mL of deionized water; simultaneously, 75.0 mL of a concentrated ammonium hydroxide solution (14.5 M) was added via the other addition funnel maintaining a pH of >10 in the round-bottomed flask during the addition of reagents. The mixture was stirred vigorously during addition, and for 2 h following completion of addition.

The white precipitate that formed was isolated by filtration, washed twice with 100 mL portions of deionized water, and dried in a vacuum oven overnight at 100° C. Yield of dry product, the initial catalyst composition, was 18.74 g. X-ray powder diffraction peaks expected for a compound of approximate formula $Sr_8Ca_2(PO_4)_6(OH)_2$. BET Surface Area: 52.2 m²/g. TEM pictures showed the product was primarily $Sr_8Ca_2(PO_4)_6(OH)_2$ rod-like nanoparticles with dimensions of from 10 to 40 nm along the small dimension to 50-300 nm in length. The material was calcined at 600° C. for 8 h in an oven.

To a 500 mL round-bottomed borosilicate glass flask was charged 9.45 g of the initial catalyst composition and 100.0 mL of a saturated solution of strontium hydroxide (1.77 g/100 ml) that was stored in a borosilicate glass bottle. The reaction mixture was refluxed under nitrogen for one hour. After cooling the base-treated product was isolated by filtration, and was then dried in a vacuum oven at 100° C. overnight yielding 9.95 g of base-treated catalyst composition as product. X-ray powder diffraction peaks expected for a compound of approximate formula $Sr_8Ca_2(PO_4)_6(OH)_2$. BET Surface Area: 35.6 m²/g. TEM pictures showed the product was primarily $Sr_6Ca_2(PO_4)_6(OH)_2$ rod-like nanoparticles with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

The calcined base-treated catalyst composition was evaluated using a similar procedure to Examples 1 through 10, but using chilled liquid sampling in solvent rather than direct gas injection into a gas chromatograph. Approximately 2.6 g of each catalyst composition was separately loaded on a stainless steel mesh support within a 18 inch×½ inch (45.7 cm×1.3 cm) outside diameter (o.d.) type 316 stainless steel tube reactor with inlets for gas and liquid feeds. The catalyst composition was then pre-conditioned in situ in the reactor by flowing nitrogen gas at 15 mL/min, initially at room temperature, raising the temperature to 400° C., and introducing the ethanol to generate reaction data. At reaction temperature nitrogen flow was set at 6 mL/min and ethanol flow at 4.0 mL/hr. The gaseous product stream was periodically sampled by condensing in a 2 ml glass vial which contained 0.5 ml n-methyl pyrrolidone (NMP) at −10 C. This diluted sample was then injected on an Agilent™ 6890 CC equipped with flame ionization and mass selective detectors. The results are tabulated in Table 16 and shown graphically in FIG. 2 as the total conversion of ethanol to products as a function of time. The lifetime shown of over 1600 hours represents only a gradual decline in activity over this period of continuous feed.

TABLE 16

Lifetime Data for the Base-Treated Catalyst Composition of Example 15.

| Time (hours) | EtOH Conv (%) |
|---|---|
| 95 | 35.1 |
| 100 | 35.6 |
| 287 | 35.5 |
| 455 | 35.6 |
| 767 | 32.5 |

TABLE 16-continued

Lifetime Data for the Base-Treated
Catalyst Composition of Example 15.

| Time (hours) | EtOH Conv (%) |
|---|---|
| 983 | 30.3 |
| 1319 | 30.5 |
| 1326 | 28.2 |
| 1343 | 30.8 |
| 1367 | 28.5 |
| 1439 | 30.0 |
| 1535 | 31.1 |

Example 16

Synthesis of Nanocrystalline $Sr_{10}(PO_4)_6(OH)_2$, Base Treatment with $Sr(OH)_2$, Incorporation of 0.05 Weight Percent Nickel Metal, and Use of the Base-Treated, Nickel-Containing Catalyst Composition to Produce a Reaction Product Comprising 1-Butanol This Example illustrates the use of a base-treated catalyst composition comprising a strontium hydroxyapatite and nickel to produce a reaction product comprising 1-BuOH.

The catalyst precursor $Sr_{10}(PO_4)_6(OH)_2$ was prepared and treated with $Sr(OH)_2$ base by a procedure similar to that described in Example 1, and calcined at 600° C. for 8 h. In a nitrogen-filled glove box, 7.0 g of this material was placed into a round-bottomed flask. To this was added 0.164 g of bis($\eta^2,\eta^2$-cyclooctadiene)nickel that had been dissolved in 50 mL of dry, deoxygenated toluene. This was stirred at room temperature under nitrogen for one hour whereupon the solution was decolorized indicating production of a nickel-containing strontium hydroxyapatite. The product was then isolated by filtration and dried in a vacuum oven at 150° C. for 2 h. Catalyst composition preparation and testing was done as described in Example 1. The nickel-containing catalyst composition exhibited a much higher conversion of ethanol, with a significant increase in other compounds including methyl benzene methanol (7%) and benzene propanol (0.7%), compared to similar catalyst compositions without nickel (Example 1). Reaction mixtures comprising 1-butanol and these compounds can be useful as fuel components.

TABLE 17

Ethanol Conversion and Product Selectivity Data for Example 16.

| Elapsed Time (hrs) | EtOH Conv. (%) | BuOH Sel. (%) | Low Boilers Sel. (%) | Total Alcohol Sel. (%) |
|---|---|---|---|---|
| 0.0 | 59.95 | 31.15 | 15.10 | 55.60 |
| 0.7 | 55.61 | 32.64 | 12.99 | 56.83 |
| 1.4 | 54.75 | 33.23 | 12.00 | 58.22 |
| 2.0 | 54.48 | 34.16 | 12.24 | 58.16 |

Example 17

Synthesis of Nanocrystalline $Sr_8Ba_2(PO_4)_6(OH)_2$, Base Treatment with $Ba(OH)_2$ to Produce a Base-Treated Catalyst Composition and Use of the Base-Treated Catalyst Composition to Produce a Reaction Product Comprising 1-Butanol This Example illustrates the use of a base-treated catalyst composition comprising a strontium- and barium-hydroxyapatite to produce a product comprising 1-butanol, and a process for making the base-treated catalyst composition.

A three-necked round-bottomed flask equipped with a pH probe and two inlets for syringe pump tubing was charged with 22.598 g of strontium acetate and 6.964 g of barium acetate dissolved in 250.0 mL of deionized water. To this was added via syringe pump 15.58 mL of a 5.24 M solution of phosphoric acid at a rate of 1.039 mL/min. Simultaneously, 75.0 mL of concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously during addition, and for 2 h following completion of addition. The former procedures were done under ambient room temperature conditions.

The white precipitate that formed was isolated by filtration, washed twice with 100 mL portions of deionized water, and dried in a vacuum oven overnight at 100° C. The yield of product was 17.8 g. The X-ray powder diffraction pattern for this material indicated the presence of a phase of approximate formula $Sr_8Ba_2(PO_4)_6(OH)_2$. The BET Surface Area was 62.1 m²/g. TEM pictures showed this product was primarily $Sr_8Ba_2(PO_4)_6(OH)_2$ rod-like nanocrystals with dimensions of from 10 to 40 nm along the small dimension to 50-300 nm in length. The material was calcined at 600° C. for 8 h in an oven.

5.0 g of the calcined material was then placed into a PFA Teflon® round-bottomed flask with 52.6 ml of a solution of $Ba(OH)_2$ (4.59 g of barium hydroxide octahydrate in 100 mL of deionized water) that was stored in a polystyrene bottle. This was stirred at 100° C. under an atmosphere of nitrogen for one hour. After cooling to room temperature, the product was isolated by filtration. It was then dried in a vacuum oven at 100° C. overnight yielding 5.44 g of solid. The base-treated product was not washed with water after filtration and before drying. The X-ray powder diffraction pattern for this material indicated the presence of a phase of approximate formula $Sr_8Ba_2(PO_4)_6(OH)_2$. The BET Surface Area was 41.5 m²/g. TEM pictures showed this product was primarily $Sr_8Ba_2(PO_4)_6(OH)_2$ rod-like nanocrystals with dimensions of from 10 to 40 nm along the small dimension to 50-300 nm in length.

The base-treated catalyst composition was pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

This calcined base-treated catalyst composition was evaluated using the procedure of Example 1, but with 2.79 grams of catalyst composition. The results are shown in Table 18.

TABLE 18

Ethanol Conversion and Product Selectivity Data for Example 17.

| Elapsed Time (hrs) | EtOH Conv. (%) | BuOH Sel. (%) | Low Boilers Sel. (%) | Total Alcohol Sel. (%) |
|---|---|---|---|---|
| 0.0 | 22.92 | 42.88 | 27.39 | 57.19 |
| 2.7 | 24.88 | 42.86 | 23.71 | 58.32 |

TABLE 18-continued

Ethanol Conversion and Product Selectivity Data for Example 17.

| Elapsed Time (hrs) | EtOH Conv. (%) | BuOH Sel. (%) | Low Boilers Sel. (%) | Total Alcohol Sel. (%) |
|---|---|---|---|---|
| 5.7 | 24.70 | 42.97 | 22.56 | 58.95 |
| 9.7 | 25.32 | 43.80 | 21.65 | 60.26 |
| 14.8 | 25.15 | 45.01 | 21.44 | 61.54 |

Although particular embodiments of the present invention have been described in the foregoing description, it will be understood by those skilled in the art that the invention is capable of numerous modifications, substitutions, and rearrangements without departing from the spirit of essential attributes of the invention. Reference should be made to the appended claims, rather than to the foregoing specification, as indicating the scope of the invention.

What is claimed is:

1. A process comprising the step of:
contacting an initial catalyst composition comprising a hydroxyapatite based on unary, binary, tertiary, and quaternary combinations of magnesium, calcium, strontium, and barium cations, which is represented by the structure of Formula (III):

$$(M_m M'_n M''_p M'''_q)_5(PO_4)_3(OH) \quad \text{(III)}$$

where
M is Mg; M' is Ca; M" is Sr; M''' is Ba;
m is any number between 0 and 1 inclusive;
n is any number between 0 and 1 inclusive;
p is any number between 0 and 1 inclusive;
q is any number between 0 and 1 inclusive; and
m+n+p+q=1
with a base at a temperature from about 25° C. to about 300° C. for a time of about 1 minute to about 24 hours to produce a base-treated catalyst composition.

2. The process of claim 1, wherein the base comprises an aqueous solution of a metal hydroxide $Q(OH)_f$ where f is 1 to 3 inclusive and
Q is at least one metal selected from the group consisting of Mg, Ca, Sr and Ba, and
wherein the aqueous solution has a pH greater than about 11.

3. The process of claim 1, wherein the initial catalyst composition further comprises a metal phosphate of Formula (II):

$$(M_a M'_b M''_c M'''_d)_3(PO_4)_2 \quad \text{(II)}$$

where M is Mg; M' is Ca; M" is Sr; M''' is Ba;
a is any number between 0 and 1 inclusive;
b is any number between 0 and 1 inclusive;
c is any number between 0 and 1 inclusive;
d is any number between 0 and 1 inclusive; and
a+b+c+d=1.

4. The process of claim 1, wherein the initial catalyst composition further comprises at least one anionic additive selected from the group consisting of carbonate, silicate, aluminate, arsenate, vanadate, sulfate, and borate.

5. The process of claim 1, wherein m is 1, n is 0, p is 0, and q is 0.

6. The process of claim 1, wherein m is 0, n is 0, p is 1, and q is 0.

7. The process of claim 1, wherein m is 0, n is 0, p is 0, and q is 1.

8. The process of claim 1, wherein m is any number between 0 and 1 inclusive; n is any number from 0 to less than 0.5; p is 0; and q is 0.

9. The process of claim 1, wherein m is any number between 0 and 1 inclusive; n is 0; p is any number between 0 and 1 inclusive; and q is 0.

10. The process of claim 1, wherein m is any number between 0 and 1 inclusive; n is 0; p is 0; and q is any number between 0 and 1 inclusive.

11. The process of claim 1, wherein m is 0; n is any number from 0 to less than 0.5; p is any number between 0 and 1 inclusive; and q is 0.

12. The process of claim 1, wherein m is 0; n is any number from 0 to less than 0.5; p is 0; and q is any number between 0 and 1 inclusive.

13. The process of claim 1, wherein m is 0; n is 0; p is any number between 0 and 1 inclusive; and q is any number between 0 and 1 inclusive.

14. The process of claim 1, wherein the initial catalyst composition comprises an isolated solid.

15. The process of claim 1, wherein the initial catalyst composition is calcined before treatment with base.

16. The process of claim 1, wherein the base-treated catalyst composition is washed with a total of about 0 to about 20 mL of water per g of solid.

* * * * *